US011525832B2

United States Patent
Borrebaeck et al.

(10) Patent No.: US 11,525,832 B2
(45) Date of Patent: *Dec. 13, 2022

(54) PROTEIN SIGNATURE/MARKERS FOR THE DETECTION OF ADENOCARCINOMA

(71) Applicant: IMMUNOVIA AB, Lund (SE)

(72) Inventors: Carl Arne Krister Borrebaeck, Lund (SE); Lars Bertil Christer Wingren, Sodra Sandby (SE)

(73) Assignee: IMMUNOVIA AB, Lund (SE)

( * ) Notice: Subject to any disclaimer, the term of this patent is extended or adjusted under 35 U.S.C. 154(b) by 251 days.

This patent is subject to a terminal disclaimer.

(21) Appl. No.: 16/578,768

(22) Filed: Sep. 23, 2019

(65) Prior Publication Data

US 2020/0018760 A1 Jan. 16, 2020

Related U.S. Application Data

(63) Continuation of application No. 15/589,084, filed on May 8, 2017, now abandoned, which is a continuation of application No. 12/593,448, filed as application No. PCT/GB2008/001090 on Mar. 25, 2008, now abandoned.

(30) Foreign Application Priority Data

Mar. 27, 2007 (GB) .................................. 0705876
Jun. 25, 2007 (GB) .................................. 0712181

(51) Int. Cl.
*G01N 33/574* (2006.01)

(52) U.S. Cl.
CPC ............................. *G01N 33/57438* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. | |
| 4,486,530 A | 12/1984 | David et al. | |
| 5,856,090 A | 1/1999 | Epstein | |
| 6,258,540 B1 | 7/2001 | Lo et al. | |
| 6,355,623 B2 | 3/2002 | Seidman | |
| 7,354,584 B2 | 4/2008 | Reed et al. | |
| 8,632,983 B2 | 1/2014 | Haab et al. | |
| 11,320,436 B2 * | 5/2022 | Delfani | C07K 16/38 |
| 2004/0110219 A1 | 6/2004 | Buccholz et al. | |
| 2004/0213791 A1 | 10/2004 | Bander et al. | |
| 2004/0219572 A1 | 11/2004 | Chen et al. | |
| 2005/0095611 A1 | 5/2005 | Chan et al. | |
| 2005/0132427 A1 | 6/2005 | Nakamura et al. | |
| 2005/0260639 A1 | 11/2005 | Nakamura et al. | |
| 2007/0212738 A1 | 9/2007 | Haley et al. | |
| 2009/0291434 A1 | 11/2009 | Cowens et al. | |
| 2012/0264634 A1 | 10/2012 | Amersdorfer et al. | |
| 2013/0260388 A1 | 10/2013 | Shen et al. | |
| 2016/0033511 A1 | 2/2016 | Pannell et al. | |
| 2017/0153239 A1 | 6/2017 | Paik et al. | |
| 2018/0136231 A1 | 5/2018 | Borrebaeck et al. | |
| 2019/0128891 A1 * | 5/2019 | Borrebaeck | C12Q 1/6886 |
| 2019/0382849 A1 * | 12/2019 | Borrebaeck | G16H 50/30 |
| 2020/0011872 A1 * | 1/2020 | Borrebaeck | G01N 33/57484 |
| 2022/0026431 A1 * | 1/2022 | Delfani | C07K 16/18 |

FOREIGN PATENT DOCUMENTS

| | | |
|---|---|---|
| CA | 1202235 | 3/1986 |
| CA | 2904973 A1 | 9/2014 |
| CN | 1851455 | 10/2006 |
| CN | 101246176 A | 8/2008 |
| CN | 101451975 | 6/2009 |
| CN | 101460849 A | 6/2009 |
| CN | 101613748 A | 12/2009 |
| CN | 101676300 A | 3/2010 |
| CN | 101743327 A | 6/2010 |
| CN | 101854946 A | 10/2010 |
| CN | 101880707 A | 11/2010 |
| CN | 102201038 A | 9/2011 |
| CN | 102279264 A | 12/2011 |
| CN | 102286464 A | 12/2011 |

(Continued)

OTHER PUBLICATIONS

Sumiyoshi, K., et al., "Biosynthesis and Secretion of MHC Class III Gene Products (Complement C4 and Factor B) in the Exocrine Pancreas" J. Gastroenterol. (1997) 32:367-373.

(Continued)

*Primary Examiner* — Peter J Reddig
(74) *Attorney, Agent, or Firm* — Robert C. Netter, Jr.; Dann, Dorfman, Herrell & Skillman

(57) ABSTRACT

The present invention provides a method for determining the presence of pancreatic adenocarcinoma in an individual and/or for determining the survival time of an individual afflicted with pancreatic adenocarcinoma comprising the steps of: (a) providing a serum or plasma sample to be tested; and (b) determining a protein signature of the test sample by measuring the presence and/or amount in the test sample of one or more selected proteins; wherein the presence and/or amount in the test sample of one or more proteins selected from the group defined in Table 1 is indicative of the presence of pancreatic adenocarcinoma. The invention also provides an array and a kit suitable for use in the methods of the invention.

9 Claims, 10 Drawing Sheets

(56) References Cited

FOREIGN PATENT DOCUMENTS

| | | |
|---|---|---|
| CN | 111171053 A | 5/2020 |
| EP | 1736780 A1 | 12/2006 |
| EP | 2148932 | 2/2010 |
| JP | 2004-248575 A | 9/2004 |
| JP | 2007-051880 A | 3/2007 |
| JP | 2015-033381 A | 2/2015 |
| KR | 10-2006-0112258 A | 10/2006 |
| KR | 20110056564 A | 5/2011 |
| RU | 2421149 C2 | 6/2011 |
| WO | 98/37186 A1 | 8/1998 |
| WO | 01/06262 A1 | 1/2001 |
| WO | 2004/031412 A2 | 4/2004 |
| WO | 2004055519 A2 | 7/2004 |
| WO | 2004094458 A2 | 11/2004 |
| WO | 2005/004809 A2 | 1/2005 |
| WO | 2005013682 A2 | 2/2005 |
| WO | 2005/063812 | 7/2005 |
| WO | 2006/110581 A2 | 10/2006 |
| WO | 2006/110599 A2 | 10/2006 |
| WO | 2006/113210 | 10/2006 |
| WO | 2006/121892 | 11/2006 |
| WO | 2007/045966 A2 | 4/2007 |
| WO | 2007/107774 A2 | 9/2007 |
| WO | 2007/122820 A1 | 11/2007 |
| WO | 2008/021174 A2 | 2/2008 |
| WO | 2008/079269 A2 | 7/2008 |
| WO | 2008/117067 A2 | 10/2008 |
| WO | 2008/127718 A2 | 10/2008 |
| WO | 2008/139169 A1 | 11/2008 |
| WO | 2008/143533 A1 | 11/2008 |
| WO | 2009/006439 A1 | 1/2009 |
| WO | 2009/062050 A2 | 5/2009 |
| WO | 2009/068857 A1 | 6/2009 |
| WO | 2009/111067 A2 | 9/2009 |
| WO | 2010/023458 A1 | 3/2010 |
| WO | 2010/102195 A2 | 9/2010 |
| WO | 2010/105235 A2 | 9/2010 |
| WO | 2011/010969 A1 | 1/2011 |
| WO | 2012/021407 A2 | 2/2012 |
| WO | 2012/120288 A2 | 9/2012 |
| WO | 2013/052480 A1 | 4/2013 |
| WO | 2013/106844 A2 | 7/2013 |
| WO | 2014/089241 A2 | 6/2014 |
| WO | 2014/141683 A1 | 9/2014 |
| WO | 2014/160499 A2 | 10/2014 |
| WO | 2015/067969 A2 | 5/2015 |
| WO | 2015/112429 A1 | 7/2015 |
| WO | 2015/157557 A1 | 10/2015 |
| WO | 2015/171736 A2 | 11/2015 |
| WO | 2016/124947 A1 | 8/2016 |
| WO | 2017/008388 A1 | 1/2017 |
| WO | 2017/008389 A1 | 1/2017 |
| WO | 2017/050939 A2 | 3/2017 |
| WO | 2017/194613 A2 | 11/2017 |
| WO | 2018/141804 A1 | 8/2018 |
| WO | 2019/232361 A1 | 12/2019 |

OTHER PUBLICATIONS

Mantovani, L.T., et al., "Folate Binding Protein Distribution in Normal Tissues and Biological Fluids from Ovarian Carcinoma Patients as Detected by the Monoclonal Antibodies MOv18 and MOv19" Eur. J. Cancer (1994) 30A (3):363-369.

Zhang, Z., et al., "Cancer Proteomics: In Pursuit of "True" Biomarker Discovery" Cancer Epidemiol. Biomarkers Prev. (2005) 14(10):2283-6.

Ballehaninna, U.K., et al., "Serum CA 19-9 as a Biomarker for Pancreatic Cancer—A Comprehensive Review" Indian J. Surg. Oncol. (2011) 2(2):88-100.

Bettac, L., "Complement in Pancreatic Disease—Perpetrator or Savior?" Front. Immunol. (2017) 8:15.

Yoneyama, T., et al., "Identification of IGFBP2 and IGFBP3 As Compensatory Biomarkers for CA19-9 in Early-Stage Pancreatic Cancer Using a Combination of Antibody-Based and LC-MS/MS-Based Proteomics" PLoS ONE (2016) 11(8):e0161009.

Felder, M., et al., "MUC16 (CA125): tumor biomarker to cancer therapy, a work in progress" Molecular Cancer (2014) 13:129.

Ferguson, T.W., et al., "Cystatin C as a biomarker for estimating glomerular filtration rate" Curr. Opin. Nephrol. Hypertens. (2015) 24:295-300.

Steinberg, W., "The Clinical Utility of the CA 19-9 Tumor-Associated Antigen" Am. J. Gastroenterol. (1990) 85(4):350-355.

Gronborg, M., et al., "Comprehensive Proteomic Analysis of Human Pancreatic Juice" J. Proteome Res. (2004) 3:1042-1055.

Haeno, H., et al., "Computational Modeling of Pancreatic Cancer Reveals Kinetics of Metastasis Suggesting Optimum Treatment Strategies" Cell (2012) 148:362-375.

Hippisley-Cox, J., et al., "Identifying patients with suspected pancreatic cancer in primary care: derivation and validation of an algorithm" Br. J. Gen. Pract. (2012) 62(594):e38-e45.

Ilic, M., et al., "Epidemiology of pancreatic cancer" World J. Gastroenterol. (2016) 22(44): 9694-9705.

Kauffmann, A., et al., "Microarray data quality control improves the detection of differentially expressed genes" Genomics (2010) 95:138-142.

Kauffmann, A., et al., "arrayQualityMetrics—a bioconductor package for quality assessment of microarray data" Bioinformatics (2009) 25(3):415-416.

Keane, M.G., et al., "A case—control study comparing the incidence of early symptoms in pancreatic and biliary tract cancer" BMJ Open (2014) 4:e005720.

Keane, M.G., et al., "Sociodemographic Trends in the Incidence of Pancreatic and Biliary Tract Cancer in UK Primary Care" PLoS ONE (2014) 9(9): e108498.

Kenner, B.J., et al., "Early Detection of Pancreatic Cancer—a Defined Future Using Lessons From Other Cancers: A White Paper" Pancreas (2016) 45(8):1073-9.

Kloppel, G., et al., "Chronic Pancreatitis and the Differential Diagnosis Versus Pancreatic Cancer" Arch. Pathol. Lab. Med. (2009) 133:382-387.

Kos, J., et al., "Cysteine proteinases and their inhibitors in extracellular fluids: Markers for diagnosis and prognosis in cancer" Intl. J. Biol. Markers (2000) 15(1):84-89.

Lacroix, M., et al., "Residue Lys57 in the Collagen-Like Region of Human L-Ficolin and Its Counterpart Lys47 in H-Ficolin Play a Key Role in the Interaction with the Mannan-Binding Lectin-Associated Serine Proteases and the Collectin Receptor Calreticulin" J. Immunol. (2009) 182:456-465.

Stapley, S., et al., "The risk of pancreatic cancer in symptomatic patients in primary care: a large case-control study using electronic records" Brit. J. Cancer (2012) 106:1940-1944.

Liu, L., et al., "The clinical utility of CA125/MUC16 in pancreatic cancer: A consensus of diagnostic, prognostic and predictive updates by the Chinese Study Group for Pancreatic Cancer (CSPAC)" Intl. J. Oncol. (2016) 48:900-907.

Shi, W., et al., "Osteoprotegerin is up-regulated in pancreatic cancers and correlates with cancer-associated new-onset diabetes" BioScience Trends (2014) 8(6):322-326.

Ni, X.G., et al., "The Ubiquitin-Proteasome Pathway Mediates Gelsolin Protein Downregulation in Pancreatic Cancer" Mol. Med. (2008) 14(9-10): 582-589.

Shahbazi, S., et al., "Characterization of the interaction between von Willebrand factor and osteoprotegerin" J. Thrombosis Haemostasis (2007) 5:1956-1962.

Sall, A., et al., "Generation and analyses of human synthetic antibody libraries and their application for protein microarrays" Protein Engineering Design Selection (2016) 29(10):427-437.

Aptamer, Wikipedia: The Free Encyclopedia, Wikimedia Foundation, Available from https://en.wikipedia.org/wiki/Aptamer [Retrieved Feb. 23, 2012].

Crnogorac-Jurcevic, et al., "Proteomic Analysis of Chronic Pancreatitis and Pancreatic Adenocarcinoma" Gastroenterology, (2005) 129:1454-1463.

Fujiwara, et al. "Transforming activity of the lymphotoxin-B receptor revealed by expression screening" (2005) Biochem. & Biophys. Res. Com., 338(2):1256-1262.

(56) References Cited

OTHER PUBLICATIONS

Jiang, et al., "Angiomotin and angiomotin like proteins, their expression and correlation with angiogenesis and clinical outcome in human breast cancer" BMC Cancer (2006) 6:16.
Li, et al., "Cyclophilin A Is Overexpressed in Human Pancreatic Cancer Cells and Stimulates Cell Proliferation through CD147" Cancer (2006) 106:2284-2294.
Li, et al., "Expression of Syk and VEGF-D Protein in Pancreatic Cancer and Their Clinical Signfiicance" Chinese J. Cancer Prevention & Treatment (2008) 15(15):1166-1168 [ABSTRACT only].
Meng, et al., "Overexpression of NDC80 is correlated with prognosis of pancreatic cancer and regulates cell proliferation" Am J Cancer Res (2015) 5(5):1730-1740.
Monti, et al., "The CC Chemokine MCP-1/CCL2 in Pancreatic Cancer Progression: Regulation of Expression and Potential Mechanisms of Antimalignant Activity" Cancer Res, (2003) 63:7451-7461.
Pauly, et al., "Protein Expression Profiling of Formalin-Fixed Paraffin-Embedded Tissue Using Recombinant Antibody Microarrays" Journal of Proteome Research (2013) 12(12):5943-5953.
Pepe, et al., "Phases of Biomarker Development for Early Detection of Cancer" J. Nat. Cancer Inst. (2001) 93(14):1054-1061.
Szajda, et al., "Carbohydrate markers of pancreatic cancer" Biochem Society Trans. (2011) 39(1):340-3.
Xie, et al. (2006) "Mining of microarray, proteomics, and clinical data for improved identification of chronic fatigue syndrome" Critical Assessment of Microarray Data Analysis Conference, Durham, North Carolina.
Zhang, et al., "Expression of c-erbB-2 oncogene protein, epidermal growth factor receptor, and TGF-B1 in human pancreatic ductal adenocarcinoma" Hepatobiliary & Pancreatic Diseases International (2002) 1:620-623.
Zhou, et al., "Clinical Research and Empirical Study of Combination Treatment with Gemcitabine Chemotherapy and Huai'er Granula on Pancreatic Cancer" Master's Thesis Full-Text Database, Medicine and Health Sciences, (2009) 5:E72-130 [Abstract only].
Zhao, et al. "Comparative Serum Glycoproteomics Using Lectin Selected Sialic Acid Glycoproteins with Mass Spectrometric Analysis: Application to Pancreatic Cancer Serum" (2006) J. Proteome Res. 5:1792-1802.
NCBI entry for C1—Complement C1 Inhibitor Protein—MeSH—NCBI (2006) (available from http://www.ncbi.nlm.nih.gov/mesh/68050718).
Kang, et al. "Normal C1 inhibitor mRNA expression level in type I hereditary angioedema patients: newly found C1 inhibitor gene mutations" Allergy (2006) 61:260-264.
Grzesiak, et al. "The Integrin-Extracellular Matrix Axis In Pancreatic Cancer" Pancreas (2007) 35, No. 4:293-301.
Grizzle, et al. "Abstract 2732: Multiplex Immunoanalysis of Cytokines in EUS-FNAs and in Plasma to Detect Pancreatic Cancer" Cancer Res. (2010) 70(8 Suppl.):Abstract 2732.
Al-Rawi, et al., "Aberrant expression of interleukin-7 (IL-7) and its signalling complex in human breast cancer" Eur. J. Cancer (2004) 40:494-502.
Wenke, et al. "Expression of integrin alpha10 is induced in malignant melanoma" Cellular Oncology (2007) 29:373-386.
Rutkowski, et al., "Cancer and the Complement Cascade" Mol. Cancer Res. (2010) 8:1453-65.
Derin, et al., "Serum levels of apoptosis biomarkers, survivin and TNF-alpha in nonsmall cell lung cancer" Lung Cancer (2007) 59:240-245.
Herman, et al., "Bruton tyrosine kinase represents a promising therapeutic target for treatment of chronic lymphocytic leukemia and is effectively targeted by PCI-32765" Blood (2011) 117:6287-6296.
Lambeck, et al. "Serum Cytokine Profiling as a Diagnostic and Prognostic Tool in Ovarian Cancer: A Potential Role for Interleukin 7" Clin Cancer Res. (2007) 13:2385-2391.
Huang, et al., "A biotin label-based antibody array for high-content profiling of protein expression" Cancer Genomics and Proteomics (2010) 7:129-142.
Budman, et al., "Biomarkers for Detection and Surveillance of Bladder Cancer" CUAJ (2008) 2,3:212-221.
Chu, D., et a. "Identification and screening of individuals at increased risk for pancreatic cancer with emphasis on known environmental and genetic factors and hereditary syndromes" JOP (2010) 11(3):203-12.
Clackson, et al., "Making antibody fragments using phage display libraries" Nature (1991) 352:624-628.
Conlon, K. et al. "Long-term survival after curative resection for pancreatic ductal adenocarcinoma" Clinicopathologic analysis of 5-year survivors. Annals of surgery (1996) 223(3):273-9.
Coussens, L., et al. "Inflammation and cancer" Nature (2002) 420(6917):860-7.
Daugherty, et al., "Antibody affinity maturation using bacterial surface display" Protein Eng, (1998) 11, 9:825-32.
Daugherty, et al., "Development of an optimized expression system for the screening of antibody libraries displayed on the *Escherichia coli* surface" Protein Eng, (1999) 12, 7:613-21.
Dexlin-Mellby, L., et al. "Tissue proteomic profiling of preeclamptic placenta tissue using recombinant antibody microarrays" Proteomics—Clinical Applications (2010) 4(10-11):794-807.
Ducreux, et al., (2015) "Cancer of the pancreas: ESMO Clinical Practice Guidelines for diagnosis, treatment and follow-up" Annals of Oncology, 26 (Supplement 5): v56-v68.
Duffy, M., et al. J. "Tumor markers in pancreatic cancer: a European Group on Tumor Markers (EGTM) status report" Ann Oncol (2010) 21(3):441-7.
Duraker, N., et al. "CEA, CA 19-9, and CA 125 in the differential diagnosis of benign and malignant pancreatic diseases with or without jaundice" Journal of Surgical Oncology (2007) 95(2):142-7.
Eisen, M., et al. "Closter analysis and display of genome-wide expression patterns" Proc Natl Acad Sci USA. (1998) 95: 14863-14868.
Ellmark, P., et al. "Identification of protein expression signatures associated with Helicobacter pylori infection and gastric adenocarcinoma using recombinant antibody microarrays" Mol Cell Proteomics (2006) 5:1638-46.
Johnson, W., et al. "Adjusting batch effects in microarray expression data using empirical Bayes methods" Biostatistics (2007) 8(1):118-27.
Faca, V., et a. "A mouse to human search for plasma proteome changes associated with pancreatic tumor development" PLoS Medicine (2008) 5:e123.
Feldmann, G., et al. "Cyclin-dependent kinase inhibitor Dinaciclib (SCH727965) inhibits pancreatic cancer growth and progression in murine xenograft models" Cancer Biology & Therapy (2011) 12(7):598-609.
Firpo, M., et al. "Improved diagnosis of pancreatic adenocarcinoma using haptoglobin and serum amyloid A in a panel screen" World Journal of Surgery (2009) 33(4):716-22.
FMA (Foundational Model of Anatomy) browser (2019) accessible at http://xiphoid.biostr.washington.edu/fma/index.html.
Fraker, et al., Protein and Cell Membrane Iodinations with a Sparingly Soluble Chloroamide, 1,3,4,6-tetrachloro-3a,6a-diphenylglycoluril: Biochem. Biophys. Res. Comm. (1978) 80:849-57.
Freelove, et al. "Pancreatic Cancer: Diagnosis and Management" American Family Physician (2006) 73(3):485-492.
Frick, V. et al. "Enhanced ENA-78 and IL-8 expression in patients with malignant pancreatic diseases" Pancreatology (2008) 8(4-5):488-497.
Fry, L., et al. "Molecular markers of pancreatic cancer: development and clinical relevance" Langenbecks Arch Surg. (2008) 393(6):883-890.
Furukawa, H., et al. "Clinicopathologic features of small pancreatic adenocarcinoma. A collective study". Cancer. (1996) 78(5):986-90.
Gabitass, R., et al. "Elevated myeloid-derived suppressor cells in pancreatic, esophageal and gastric cancer are an independent prog-

(56) References Cited

OTHER PUBLICATIONS nostic factor and are associated with significant elevation of the Th2 cytokine interleukin-13" Cancer Immunology, Immunotherapy: CII. (2011) 60(10):1419-30.
Galasso, D., et al. "Pancreatic cancer: diagnosis and endoscopic staging". Eur Rev Med Pharmacol Sci, (2010) 14(4):375-85.
Gangi, S., et al. Time interval between abnormalities seen on CT and the clinical diagnosis of pancreatic cancer: retrospective review of CT scans obtained before diagnosis AJR (2004) 182:897-903.
Gao, W., et al. "Distinctive serum protein profiles involving abundant proteins in lung cancer patients based upon antibody microarray analysis" BMC Cancer (2005) 5:110.
Gerdtsson, A., et al. "A Multicenter Trial Defining a Serum Protein Signature Associated with Pancreatic Ductal Adenocarcinoma" Int J Proteomics (2015) 2015:587250.
Ghatnekar, O., et al. "Modelling the benefits of early diagnosis of pancreatic cancer using a biomarker signature" International Journal of Cancer Journal International du Cancer (2013) 133(10):2392-7.
Gunneriusson, et al., "*Staphylococcal* Surface Display of Immunoglobulin A (IgA)- and IgE-Specific In Vitro-Selected Binding Proteins (Affibodies) Based on *Staphylococcus aureus* Protein A": Appl Environ Microbiol (1999) 65, 9:4134-40.
Gupta, S., et al. "Challenges and prospects for biomarker research: a current perspective from the developing world" Biochimica et Biophysica Acta. (2014) 1844(5):899-908.
Haab, B., et al. "Immunoassay and antibody microarray analysis of the HUPO Plasma Proteome Project reference specimens: systematic variation between sample types and calibration of mass spectrometry data" Proteomics (2005) 5(13):3278-91.
Haab, B., et al., "Protein microarrays for highly parallel detection and quantitation of specific proteins and antibodies in complex solutions" Genome Biology (2001) 2(2):research0004.1-0004.13.
Hanes, et al., "In vitro selection and evolution of functional proteins by using ribosome display" Proc Natl Acad Sci USA (1997) 94, 10:4937-42.
He, et al., "Antibody-ribosome-mRNA (ARM) complexes as efficient selection particles for in vitro display and evolution of antibody combining sites" Nucleic Acids Res (1997) 25, 24:5132-4.
Hidalgo, M. "Pancreatic cancer" The New England Journal of Medicine (2010) 362(17):1605-17.
Honda K., et al. "Altered plasma apolipoprotein modifications in patients with pancreatic cancer: protein characterization and multi-institutional validation" PLoS One. (2012) 7(10):e46908.
Hou, J., et al. "Estrogen-sensitive PTPRO expression represses hepatocellular carcinoma progression by control of STAT3" Hepatology (2013) 57(2):678-88.
Meyer, et al., "CRAN—Package e1071" (2019) available at http://cran.r-project.org/web/packages/e1071/index.html.
Huang, Y., et al. "PTPRO promoter methylation is predictive of poorer outcome for HER2-positive breast cancer: indication for personalized therapy" Journal of Translational Medicine (2013)11:245.
Huston, et al., "Protein engineering of antibody binding sites: Recovery of specific activity in an anti-digoxin single-chain Fv analogue produced in *Escherichia coli*" Proc. Natl. Acad. Sci. USA (1988) 85:5879-83.
Ihaka, et al. "R: A language for data analysis and graphics" J. Comp. Graph. Stat. (1996) 5:299-314.
Ingvarsson, J., et al. "Design of recombinant antibody microarrays for serum protein profiling: targeting of complement proteins" Journal of Proteome Research (2007) 6:3527-36.
Ishikawa, O., et al. "Minute carcinoma of the pancreas measuring 1 cm or less in diameter—collective review of Japanese case reports" Hepato-gastroenterology (1999) 46:8-15.
Itakura, J., et al. "Enhanced expression of vascular endothelial growth factor in human pancreatic cancer correlates with local disease progression" Clinical Cancer Research: An Official Journal of the American Association for Cancer Research (1997) 3(8):1309-16.
Jemal, A., et al. "Cancer statistics" CA Cancer J Clin (2009)59:225-49.

Jenkins, R., et al., "Arrays for protein expression profiling: Towards a viable alternative to two-dimensional gel electrophoresis?" Proteomics, (2001) 1:13-29.
Jiang, J., et al. (2004) "Serum level of TSGF, CA242 and CA19-9 in pancreatic cancer" World Journal of Gastroenterology : WJG 10(11):1675-7.
Jimenez-Vidal, M., et al. "Nuclear-localized calcineurin homologous protein CHP1 interacts with upstream binding factor and inhibits ribosomal RNA synthesis" The Journal of Biological Chemistry (2010) 285(47):36260-6.
Jin, Q., et al. "Overexpression of CHP2 enhances tumour cell growth, invasion and metastasis in ovarian cancer" In vivo (2007) 21(4):593-8.
Kenan, et al., "In Vitro Selection of Aptamers from RNA Libraries" Methods Mol Biol (1999)118:217-31.
Kieke, et al., "Selection of functional T cell receptor mutants from a yeast surface-display library" Proc Natl Acad Sci USA (1999) 96,10:5651-6.
Konstantinou, F., et al. (2013) "Pancreatic cancer: what about screening and detection" JOP : Journal of the Pancreas 14(4):312-5.
Koopmann, J., et al. "Serum markers in patients with resectable pancreatic adenocarcinoma: macrophage inhibitory cytokine 1 versus CA19-9" Clinical Cancer Research: An Official Journal of the American Association for Cancer Research (2006) 12:442-6.
Kudo-Saito, C., et al. "CCL2 is critical for immunosuppression to promote cancer metastasis" Clinical & Experimental Metastasis (2013) 30(4):393-405.
Lal, et al., "Antibody arrays: an embryonic but rapidly growing technology" Drug Discov Today (2002)15;7 (18 Suppl): S143-9).
Lau, M., et al. (2010) "Incidence and survival of pancreatic head and body and tail Cancers: a population-based study in the United States" Pancreas 39(4):458-62.
Ling, Q., et al. "The diversity between pancreatic head and body/tail cancers: clinical parameters and in vitro models" Hepatobiliary & Pancreatic Diseases International: HBPD INT. (2013) 12(5):480-7.
Locker, G., et al. "ASCO 2006 update of recommendations for the use of tumor markers in gastrointestinal cancer" Journal of Clinical Oncology: Official Journal of the American Society of Clinical Oncology (2006) 24:5313-27.
Ma, Y., et al. (2013) "Dynamic mast cell-stromal cell interactions promote growth of pancreatic cancer" Cancer Research 73(13):3927-37.
Malvezzi, M., et al. "European cancer mortality predictions for the year" Annals of oncology (2014) 25(8):1650-6.
Marks, et al., "By-passing Immunization Human Antibodies from V-gene Libraries Displayed on Phage" J Mol Biol (1991) 222:581-97.
McDade, T., et al. "Salicylates inhibit NF-kappaB activation and enhance TNF-alpha-induced apoptosis in human pancreatic cancer cells" The Journal of Surgical Research (1999) 83(1): 56-61.
McShane, L., et al. "Reporting recommendations for tumor MARKer prognostic studies (REMARK)". Nat Clin Pract Oncol (2005) 2:416-22.
Melo, S., et al. (2015) "Glypican-1 identifies cancer exosomes and detects early pancreatic cancer" Nature 523: 177-182.
Miller, J., et al. "Antibody microarray profiling of human prostate cancer sera: antibody screening and identification of potential biomarkers" Proteomics (2003) 3(1):56-63.
Mor, G., et al., "Serum protein markers for early detection of ovarian cancer" Proc. Natl. Acad. Sci (2005) 102, 7677-7682.
Morrison, et al., "Chimeric human antibody molecules: mouse antigen-binding domains with human constant region domains" Proc. Natl. Acad. Sci. USA, (1984) 81:6851-6855.
Motiwala, T., et al. "Protein tyrosine phosphatase receptor-type O (PTPRO) exhibits characteristics of a candidate tumour suppressor in human lung cancer" Proceedings of the National Academy of Sciences of the United States of America (2004) 101(38):13844-9.
Nakano M., et al. "Site-specific analysis of N-glycans on haptoglobin in sera of patients with pancreatic cancer: a novel approach for the development of tumor markers" Int J Cancer. (2008) 122(10):2301-2309.

(56) References Cited

OTHER PUBLICATIONS

Nemoto, et al., "In vitro virus: Bonding of mRNA bearing puromycin at the 3'-terminal end to the C-terminal end of its encoded protein on the ribosome in vitro" Febs lett, (1997) 414(2):405-8.
Ni, X., et al. "The clinical value of serum CEA, CA19-9, and CA242 in the diagnosis and prognosis of pancreatic cancer" European Journal of Surgical Oncology: The Journal of the European Society of Surgical Oncology and the British Association of Surgical Oncology (2005) 31:164-9.
Olsson, N., et al. "Epitope-specificity of recombinant antibodies reveals promiscuous peptide-binding properties" Protein Science: A Publication of the Protein Society (2012) 21(12):1897-910.
Shusta, et al., "Yeast Polypeptide Fusion Surface Display Levels Predict Thermal Stability and Soluble Secretion Efficiency" J Mol Biol, (1999) 292(5):949-56.
Pannala, R., et al. "New-onset diabetes: a potential clue to the early diagnosis of pancreatic cancer" The Lancet Oncology (2009) 10(1):88-95.
Parker, L, et al. "Clinical validity of detecting K-ras mutations for the diagnosis of exocrine pancreatic cancer: a prospective study in a clinically-relevant spectrum of patients" European Journal of Epidemiology (2011) 26(3):229-36.
Pauly, F., et al. "Identification of B-cell lymphoma subsets by plasma protein profiling using recombinant antibody microarrays" Leukemia Res. (2014) 38:682-690.
Pavlickova, P., et al. "Advances in recombinant antibody microarrays" Clin. Chim. Acta. (2004) 342:17-35.
Pawlak, M., et al. "Zeptosens' protein microarrays: A novel high performance microarray platform for low abundance protein analysis" Proteomics (2002) 2:383-393.
Pelaez-Luna, M., et al. Resectability of presymptomatic pancreatic cancer and its relationship to onset of diabetes: a retrospective review of CT scans and fasting glucose values prior to diagnosis The American Journal of Gastroenterology (2007) 102(10):2157-63.
Poch, B., et al. "Systemic immune dysfunction in pancreatic cancer patients" Langenbecks Arch Surg. (2007) 392 (3):353-358.
Porta, M., et al. "Validity of the hospital discharge diagnosis in epidemiologic studies of biliopancreatic pathology" PANKRAS II Study Group. European Journal of Epidemiology (2000) 16(6):533-41.
Porta, M., et al. "Exocrine pancreatic cancer: symptoms at presentation and their relation to tumour site and stage" Clinical & Translational Oncology (2005) 7(5):189-97.
Porta, M., et al. "Serum concentrations of organochlorine compounds and K-ras mutations in exocrine pancreatic cancer" PANKRAS II Study Group. Lancet. (1999) 354(9196):2125-9.
Quackenbush, J. "Computational analysis of microarray data" Nature reviews Genetics (2001) 2(6):418-27.
Rahib, L., et al. "Projecting cancer incidence and deaths to 2030: the unexpected burden of thyroid, liver, and pancreas cancers in the United States" Cancer Research (2014) 74(11):2913-21.
Rastogi, T., et al. "Opportunities for cancer epidemiology in developing countries" Nature reviews Cancer (2004) 4(11):909-17.
Rosenwald, A.,et al. "The proliferation gene expression signature is a quantitative integrator of oncogenic events that predicts survival in mantle cell lymphoma" Cancer Cell (2003) 3, 185-197.
Rosse, et al. "A reference ontology for biomedical informatics: the Foundational Model of Anatomy" J. Biomed. Informatics (2003) 36(6):478-500.
Rustgi, A., et al. "Pancreatic cancer: novel approaches to diagnosis and therapy" Gastroenterology (2005) 129(4):1344-7.
Sanchez-Carbayo, M., et al., "Profiling Bladder Cancer Using Targeted Antibody Arrays" (2006) Am. J. Pathol. 168:93-103.
Sandstrom A., et al. "Serum proteome profiling of pancreatitis using recombinant antibody microarrays reveals disease-associated biomarker signatures" Proteomics Clinical Applications (2012) 6(9-10):486-96.
Santi, et al., "Bacteriophage Lambda Display of Complex cDNA Libraries: A New Approach to Functional Genomics" J Mol Biol, (2000) 296:497-508.

Schafer, et al. "Antibody Array Profiling Reveals Serum TSP-1 as a Marker to Distinguish Benign From Malignant Prostatic Disease" The Prostate (2007) 67:255-267.
Schervish, M., "A Review of Multivariate Analysis" Statistical Science (1987) 2(4):396-413.
Schmitz-Winnenthal, F., et al. "High frequencies of functional tumor-reactive T cells in bone marrow and blood of pancreatic cancer patients" Cancer Res. (2005) 65(21):10079-87.
Shaib, Y., et al. "The epidemiology of pancreatic cancer in the United States: changes below the surface" Alimentary Pharmacology & Therapeutics (2006) 24(1):87-94.
Shaw, V., et al. "Serum cytokine biomarker panels for discriminating pancreatic cancer from benign pancreatic disease" Molecular Cancer (2014) 13:114.
Shimizu, Y., et al. "Small carcinoma of the pancreas is curable: new computed tomography finding, pathological study and postoperative results from a single institute" Journal of Gastroenterology and Hepatology (2005) 20(10):1591-4.
Galli, C., et al. "CA 19-9: handle with care" Clin Chem Lab Med. (2013) 51(7):1369-83.
Borrebaeck, C., "Precision diagnostics: moving towards protein biomarker signatures of clinical utility in cancer" Nat Rev Cancer (2017) 17(3):199-204.
Hanash, S., et al. "Mining the plasma proteome for cancer biomarkers" Nature (2008) 452(7187):571-9.
Radon, T., et al "Identification of a Three-Biomarker Panel in Urine for Early Detection of Pancreatic Adenocarcinoma" Clin Cancer Res. (2015) 21(15):3512-21.
Mayers, J., et al. "Elevation of circulating branched-chain amino acids is an early event in human pancreatic adenocarcinoma development" Nat Med. (2014) 20(10):1193-8.
Jenkinson, C., et al. "Decreased Serum Thrombospondin-1 Levels in Pancreatic Cancer Patients Up to 24 Months Prior to Clinical Diagnosis: Association with Diabetes Mellitus" Clin Cancer Res. (2016) 22(7):1734-43.
Kim, J., et al. "Detection of eraly pancreatic ductal adenocarcinoma with thrombospondin-2 and CA19-9 blood markers" Sci. Transl. Med. (2017) 12;9(398) doi: 10.1126/scitranslmed.aah5583.
Bossuyt, P., et al. "STARD 2015: an updated list of essential items for reporting diagnostic accuracy studies" BMJ. (2015) 351:h5527.
Batabyal, P., et al. "Association of diabetes mellitus and pancreatic adenocarcinoma: a meta-analysis of 88 studies" Ann Surg Oncol. (2014) 21(7):2453-62.
Wang, F., et al. "The relationship between diabetes and pancreatic cancer" Mol Cancer. (2003) 2:4.
Lopez-Lazaro, M. "Pancreatic cancer formation is gradual" ResearchGate (2017) doi10.13140/RG.2.2.16865.92009.
Notta, F., et al. "A renewed model of pancreatic cancer evolution based on genomic rearrangement patterns" Nature (2016) 538(7625):378-82.
Chari, S., et al. "Probability of Pancreatic Cancer Following Diabetes: A Population-Based Study" Gastroenterology (2005) 129(2):504-511.
Aggarwal, G., et al. "New-onset diabetes in pancreatic cancer: A study in the primary care setting" Pancreatology (2012) 12(2):156-161.
Roberts, S., et al. "The PDZ protein discs-large (DLG): the 'Jekyll and Hyde' of the epithelial polarity proteins" FEBS J. (2012) 279(19):3549-58.
Kranjec, C., et al. "Restoration of MAGI-1 expression in human papillomavirus-positive tumor cells induces cell growth arrest and apoptosis" J Virol. (2014) 88(13):7155-69.
Lan, X., et al. "Whole-exome sequencing identifies variants in invasive pituitary adenomas" Oncol Lett. (2016)12(4):2319-28.
Huang, Y., et al. "Four genetic polymorphisms of lymphotoxin-alpha gene and cancer risk: a systematic review and meta-analysis" PLoS One (2013) 8(12):e82519.
Human Protein Atlas "Expression of LTA in cancer—The Human Protein Atlas" (2017) [Available from: http://wwwproteinatlas.org/ENSG00000226979-LTA/cancer].
Mamidi, S., et al. "The complement system in cancer: Ambivalence between tumour destruction and promotion" Immunobiology (2017) 222(1):45-54.

(56) References Cited

OTHER PUBLICATIONS

Pio, R., et al. "The role of complement in tumor growth" Adv Exp Med Biol. (2014):722:229-62.
Grande, C., et al. "Interleukin-2 for the treatment of solid tumors other than melanoma and renal cell carcinoma" Anticancer Drugs (2006) 17(1):1-12.
Nobili C., et al, "Prolonged survival of a patient affected by pancreatic adenocarcinoma with massive lymphocyte and dendritic cell infiltration after interleukin-2 immunotherapy" Report of a case. Tumori (2008) 94(3):426-30.
Stark, A., et al. "Pancreatic Ductal Adenocarcinoma" (2015) [Available from: https://www.pancreapedia.org/reviews/pancreatic-ductal-adenocarcinoma.
Leek, J., et al. "sva: Surrogate Variable Analysis" R package version 3.22.0. (2016) available at http://bioconductor.org/packages/release/bioc/html/sva.html.
Delfani, P., et al. "Technical Advances of the Recombinant Antibody Microarray Technology Platform for Clinical Immunoproteomics" PLoS One (2016) 11(7):e0159138.
Borrebaeck, C., et al. "Recombinant antibodies for the generation of antibody arrays" Methods Mol Biol (2011) 785:247-62.
Zola, "Monoclonal Antibodies: A manual of techniques" CRC Press, Florida (1988) pp. 17-61.
Hurrell, "Monoclonal Hybridoma Antibodies: Techniques and Applications" CRC Press, Florida (1982) pp. 1-57.
Thompson, et al. "Clustal W: improving the sensitivity of progressive multiple sequence alignment through sequence weighting, position-specific gap penalties and weight matrix choice" Nucl. Acid Res. (1994) 22:4673-4680.
Kunik, A., et al. (2012) "Paratome: an online tool for systematic identification of antigen-binding regions in antibodies based on sequence or structure" Nucl. Acids Res., 40:W521-W524.
Wu, et al. "An analysis of the sequences of the variable regions of Bence Jones proteins and myeloma light chains and their implications for antibody complementarity" J. Exp. Med (1970) 132:211-250.
Chothia, et al. "Canonical structures for the hypervariable regions of immunoglobulins" J. Mol. Biol., (1987) 196:901-917.
LeFranc, et al. (2003) "IMGT unique numbering for immunoglobulin and T cell receptor variable domains and Ig superfamily V-like domains" Dev. Comp. Immunol. 27:55-77.
LeFrranc, et al. "IMGT unique numbering for immunoglobulin and T cell receptor constant domains and Ig superfamily C-like domains" Dev. Comp. Immunol. (2005) 29:185-203.
Harlow, et al. "Antibodies: A Laboratory Manual" (1988) Cold Spring Harbor Press, New York, pp. 139-243.
Chothia, et al. "Conformations of immunoglobulin hypervariable regions" (1989) Nature, 342:877-883.
Siegel, R., et al. (2012) "Cancer Statistics (2012)" CA: a cancer journal for clinicians 62(1):10-29.
Skerra, et al. "Assembly of a Functional Immunoglobulin Fv Fragment in *Escherichia coli*" Science (1988) 240:1038-41.
Smith, D. "Filamentous Fusion Phage: Novel Expression Vectors That Display Cloned Antigens on the Virion Surface" Science (1985) 228:1315-7.
Soderlind, E., et al. "Recombining germline-derived CDR sequences for creating diverse single-framework antibody libraries". Nat Biotechnol. (2000) 18(8):852-856.
Sohn, T., et al. "Resected adenocarcinoma of the pancreas-616 patients: results, outcomes, and prognostic indicators" Journal of Gastrointestinal Surgery : Official Journal of the Society for Surgery of the Alimentary Tract. (2000) 4(6):567-79.
Song, M., et al. The deubiquitinylation and localization of PTEN are regulated by a HAUSP-PML network. Nature. (2008) 455(7214):813-7.
Steinhauer, C., et al. "Single framework recombinant antibody fragments designed for protein chip applications" BioTechniques Suppl (2002) 33:S38-S45.
Steinhauer, et al., "Biocompatibility of surfaces for antibody microarrays: design of macroporous silicon substrates" Anal Biochem (2005) 341:204-13.
Stoevesandt O., et al. "European and international collaboration in affinity proteomics" New biotechnology. (2012) 29(5):511-4.
Surinova, S., et al. "On the development of plasma protein biomarkers. Journal of proteome research" (2011) 10(1):5-16.
Ungefroren, H., et al. "Immunological escape mechanisms in pancreatic carcinoma" Ann N Y Acad Sci (1999) 880:243-51.
Van de Vijver, et al., "A Gene-Expression Signature as a Predictor of Survival in Breast Cancer" N. Eng. J. Med (2002) 347:1999-2009.
Ward, et al., "Binding activities of a repertoire of single immunoglobulin variable domains secreted from *Escherichia coli*" Nature (1989) 341:544-6.
Warshaw, A., et al. "Pancreatic carcinoma" N Engl J Med (1992) 326(7):455-65.
Watanabe, I., et al. "Onset symptoms and tumour locations as prognostic factors of pancreatic cancer" Pancreas. (2004) 28(2):160-5.
Wigmore, S., et al. "Cytokine regulation of constitutive production of interleukin-8 and -6 by human pancreatic cancer cell lines and serum cytokine concentrations in patients with pancreatic cancer" Int J Oncol (2002) 21(4):881-886.
Wingren, C., et al. "Antibody microarray analysis of directly labelled complex proteomes" Current Opinion in Biotechnology (2008) 19(1):55-61.
Wingren C., et al. "Design of recombinant antibody microarrays for complex proteome analysis: choice of sample labeling-tag and solid support" (2007) Proteomics 7(17):3055-65.
Wingren, C., et al. "Identification of serum biomarker signatures associated with pancreatic cancer" Cancer Research (2012) 72(10):2481-90.
Wingren, C., et al. "Microarrays based on affinity-tagged single-chain Fv antibodies: sensitive detection of analyte in complex proteomes" Proteomics (2005) 5(5):1281-91.
Wingren, et al., "High-throughput proteomics using antibody microarray" Exp. Rev. Proteomics (2004) 1:355-364.
Wingren, C., et al. "Antibody Microarrays: Current Status and Key Technological Advances" OMICS (2006) 3:411-427.
Winter, et al. "Man-made Antibodies" Nature, (1991) 349:293-299.
Winter, J., et la. "A novel survival-based tissue microarray of pancreatic cancer validates MUC1 and mesothelin as biomarkers" PLoS One (2012) 7, e40157.
Wu, T., et al. "Surgical effect of malignant tumour of body and tail of the pancreas: compare with pancreatic head cancer" Zhonghua wai ke za zhi [Chinese journal of surgery] (2007) 45(1):30-3 [Abstract Only].
Wu, Y, et al. "The impact of centering first-level predictors on individual and contextual effects in multilevel data analysis" Nursing Research (2005) 54(3):212-6.
Xia, C., et al. "GGAPs, a new family of bifunctional GTP-binding and GTPase-activating proteins" Molecular and Cellular Biology (2003) 23(7):2476-88.
Yachida, S., et al. "Distant metastasis occurs late during the genetic evolution of pancreatic cancer" Nature (2010) 467(7319):1114-7.
Yeo, et al., "Epidemiology and Risk Factors" Curr. Probl. Cancer (2002) 26:176-275.
Yu, K., et al. "Characterization of proteins in human pancreatic cancer serum using differential gel electrophoresis and tandem mass spectrometry" J Proteome Res., (2005) 4(5):1742-1751.
Zhang, H., et al. "Mass spectrometric detection of tissue proteins in plasma" Molecular & cellular proteomics: MCP (2007) 6(1):64-7.
Zhao, G., et al. "USP7 overexpression predicts a poor prognosis in lung squamous cell carcinoma and large cell carcinoma" Tumour Biol. (2015) 36:1721-1729.
American Cancer Society, "Pancreatic Cancer Stages" (2017) available at http://www.cancer.org/cancer/pancreaticcancer/detailedguide/pancreatic-cancer-staging.
Edge, et al., AJCC Cancer Staging Manual (7th ed.) (2011) Springer, New York.

(56) References Cited

OTHER PUBLICATIONS

Hanada, K., et al. "Effective screening for early diagnosis of pancreatic cancer" Best Pract Res Clin Gastroenterol. (2015) 29(6):929-939.
Chari, S., et al. "Early detection of sporadic pancreatic cancer: summative review" Pancreas (2015) 44(5):693-712.
Brentnall, T. "Progress in the Earlier Detection of Pancreatic Cancer" J Clin Oncol. (2016) 34(17):1973-4.
Lewis, et al. "Pancreatic cancer: Are "liquid biopsies" ready for prime-time?" World J Gastroenterol. (2016) 22(32):7175-7185.
Thota, et al., "Treatment of Metastatic Pancreatic Adenocarcinoma: A Review" (2014) Oncology 28(1):70-4.
Torre, L., et al. "Global cancer statistics, 2012" CA Cancer J Clin. (2015) 65(2):87-108.
Kamisawa,T. et al. "Pancreatic cancer" Lancet. (2016) 388(10039):73-85.
Okano, K., et al. "Strategies for early detection of resectable pancreatic cancer" World J Gastroenterol (2014) 20(32):11230-40.
Ryan, D., et al. "Pancreatic adenocarcinoma" N Engl J Med. (2014) 371(22):2140-1.
Zhang, H., et al. "Systematic review and meta-analysis of minimally invasive versus open approach for pancreaticoduodenectomy" Surg Endosc. (2016) 30(12):5173-84.
Matsuno, S., et al. "Pancreatic Cancer Registry in Japan: 20 years of experience". Pancreas (2004) 28(3):219-30.
Vasen, H., et al. "Benefit of Surveillance for Pancreatic Cancer in High-Risk Individuals: Outcome of Long-Term Prospective Follow-Up Studies From Three European Expert Centers" J Clin Oncol. (2016) 34(17):2010-9.
Gry, Marcus et al., "Correlations between RNA and protein expression profiles in 23 human cell lines", BMC Genomics, 10: 365 (2009).
Chen, Guoan et al., "Discordant Protein and mRNA Expression in Lung Adenocarcinomas", Molecular & Cellar Proteomics, 1: 304-313 (2002).
Alarcon-Segovia, D. et al., "Antibody penetration into living cells", Clin. exp. Immunol., 35: 364-375 (1979).
Sousa Abreu, Raquel et al., "Global signatures of protein and mRNA expression levels", Mol. BioSyst., 5:1512-1526 (2009).
Avrameas, Alexandre et al., "Polyreactive anti-DNA monoclonal antibodies and a derived peptide as vectors for the intracytoplasmic and intranuclear translocation of macromolecules", Proc Natl Acad. Sci USA, 95: 5601-5606 (1998).
Yanase, Kumiko et al., "Nuclear localizing anti-DNA antibodies enter cells via caveoli and modulate expression of caveolin and p53", 24(2): 145-151 (2005) [Abstract only].
Duell, E. et al., "Inflammation, Genetic Polymorphisms in Proinflammatory Genes TNF-A, RANTES, and CCR5, and Risk of Pancreatic Adenocarcinoma", Cancer Epidemiol Biomarkers Prev., 15(4): 726-730 (2006).
Ingvarsson, J. et al., "Detection of pancreatic cancer using antibody microarray-based serum protein profiling", Proteomics, 8: 2211-2219 (2008).
Orchekowski, R. et al., "Antibody Microarray Profiling Reveals Individual and Combined Serum Proteins Associated with Pancreatic Cancer", Cancer Res., 65(23): 11193-11202 (2005).
Phillips, C., "Study Raises Concerns about Using Cancer Cell", National Cancer Institute Cancer Bulletin, 8(23) (2011).
TawMan Gene Expression Assays Product Guide (2005).
C5-MeSH-NCB I http://www.ncbi.nlm.nih.gov/mesh, Sep. 10, 2013).
Factor b-MeSH-NCBI (MeSH—NCBI http://www.ncbi.nlm.nih.gov/mesh, Sep. 8, 2013).
GLP-1 (iHOP—Information Hyperlinked over Proteins, Sep. 11, 2013).
MCP-1 (iHOP—Information Hyperlinked over Proteins, Sep. 11, 2013).
Bloomston, M. et al., "Fibrinogen Gamma Overexpression in Pancreatic Cancer Identified by Large-scale Proteomic Analysis of Serum Samples", Cancer Research, 66(5): 2592-2599 (Mar. 2009).
Garcea, G. et al., "Molecular prognostic markers in pancreatic cancer: a systematic review", Eur. J. Cancer, 41(15): 2213-36 (Oct. 2005) (Epub Sep. 26, 2005).
Orr, F. et al., "Detection of a Complement-Derived Chemotactic Factor for Tumor Cells in Human Inflammatory and Neoplastic Effusions", Amer. J. Pathol., 110(1): 41-47 (1983).
Winikoff, S. et al., "A novel method of pancreatic cancer detection by simultaneous analysis of multiple serum markers", American Society of Clinical Oncology, 2004 Gastrointestinal Cancers Symposium, Abs. No. 166, retrieved Jan. 17, 2004: http://www.asco.org.
Wolff, Robert A. et al., , Pathology In: Kufe DW, Pollock RE, Weischselbaum RR et al.l, editors. Holland-Frei Cancer Medicine, 6th ed., Hamilton (ON): BC Decker; 2003. Available from http://www.ncbi.nim.nih.gov/books/NBK12710/.
Kobayashi, A et al., "Usefulness of Plasma Vascular Endothelial Growth Factor in the Diagnosis of Pancreatic Carcinoma", Pancreas, 31(1): 74-78 (2005).
Karayiannakis, A. et al., "Serum vascular endothelial growth factor levels in pancreatic cancer patients correlate with advanced and metastatic disease and poor prognosis", Cancer Letters, 194: 119-124 (2003).
Bellone, G. et al., Cytokine expression profile in human pancreatic carcinoma cells and in surgical specimens: implications for survival, Cancer Immunol. Immunother., 55: 684-698 (2006).
ELISA Kit and Reagent Set (http://www.genycell.es/images/productos/referencias/dkh0_.pdf, Euroclone Ltd., Jul. 30, 2012, pp. 25-27).
Geetha, A. et al., "Assessment of Immunity Status in Patients with Pancreatic Cancer", J. Clin. Biochem. Nutr., 39: 18-26 (2006).
Hornbeck, et al., "Enzyme-Linked Immunosorbent Assays (ELISA)" in Current Protocols in Molecular Biology (1991) 11.2.1-11.2.22.
Quantikine ELISA, Human VEGF Immunoassay—Package Insert, Cat. No. DVE00, SVE00, PDVE00, R&D Systems, Inc. (2019).
Paul, W.E., Fundamental Immunology, 3rd edition, Raven Press, New York (1993) pp. 292-295.
Bendig, M.M. "Humanization of Rodent Monoclonal Antibodies by CDR Grafting" Methods: A Companion to Methods in Enzymology (1995) 8:83-93.
Layton, et al., "Syk Tyrosine Kinase Acts as a Pancreatic Adenocarcinoma Tumor Suppressor by Regulating Cellular Growth and Invasion" The American Journal of Pathology (2009) 175,6:2625-2636.
Ludwig, et al., "Biomarkers in Cancer Staging, Prognosis, and Treatment Selection" Nature Reviews: Cancer (2005) 5:845-856.
Mettlin, et al. "Relative Sensitivity and Specificity of Serum Prostate Specific Antigen (PSA) Level Compared with Age-Referenced PSA, PSA Density, and PSA Change" Cancer (1994) 74,5:1615-1620.
Brawer, et al. "Measurement of Complexed PSA Improves Specificity for Early Detection of Prostate Cancer" Urology (1998) 52,3: 372-378.
Cho, et al. "WI412 Expression of Sox-11 and Sox-4 is involved in pathogenesis of solid pseudopapillary tumor in pancreas" Gastroenterology (2008) 134, 4:A-699.
Imai, et al. Database WPI Week 201518 Thomson Scientific, London, GB for JP 2015.033381 (2015).
Xiang-Yi, et al. "Advances in pancreatic cancer research: Moving towards early detection" World Journal of Gastroenterology (2014) 20, 32 :11241.
Le, et al. "Prognostic and predictive markers in pancreatic adenocarcinoma, Digestive and Liver Disease" (2015) 48, 3:223-230.
Yu, et al. "Expression profiling during mammary epithelial cell three-dimensional morphogenesis and ErbB2-mediated transformation" Molecular and Cellular Biology (2012) 32, 19:3913-3924.
The Human Protein Atlas, "Expression of PTPRO in cancer—Summary" (2015) available at http://www.proteinatlas.orb/ENSG00000151490-PTPROIcancer.
Carlsson, et al. "Antibody Microarray Based Oncoproteomics—Analysis of Breast Cancer Proteomes" Presented at 29th Annual San Antonio Breast Cancer Symposium (2006) Poster #1002.

(56) References Cited

OTHER PUBLICATIONS

Perez-Galan, et al. "The proteasome inhibitor bortezomib induces apoptosis in mantle-cell lymphoma through generation of ROS and Noxa activation independent of p53 status" Blood (2006) 107:257-264.
Gerdtsson, et al. "Plasma protein profiling in a stage defined pancreatic cancer cohort—Implications for early diagnosis" Molecular Oncology (2016) 10, 8:1306-1316.
Duffy, et al. "The Gap Junction Protein Connexin32 Interacts with the Src Homology 3/Hook Domain of Discs Large Homolog 1" Journal of Biological Chemistry (2007) 282, 13: 9789-9796.
Veronique, M, et al. "Global gene expression profiling in human lung cells exposed to cobalt" BMC Genomics (2007) 8:147.
Chen, R., et al. "Proteomics studies of pancreatic cancer" Proteomics Clin Appl (2007) 1(12):1582-1591.
Chen, R., et al. "Comparison of pancreas juice proteins from cancer versus pancreatitis using quantitative proteomic analysis" Pancreas (2007) 34(1):70-79.
Barak, et al. "Serum inflammatory cytokines, complement components, and soluble interleukin 2 receptor in primary biliary cirrhosis" J Autoimmun (2009) 33(3-4):178-82.
Chen, et al. "The relationship between CD4- CD8- T cells in the peripheral blood of patients with pancreatic carcinoma and IL-4, IFN-gamma levels" Chinese Journal of Surgery (2009) 47,13:995-998, [ABSTRACT only].
Suemizu, et al. "Identification of a key molecular regulator of liver metastasis in human pancreatic carcinoma using a novel quantitative model of metastasis in NOD/SCID/γcnull (NOG) mice", Intl. J. Oncol. (2007) 31:741-751.
Okada, et al. "Elevated Serum Interleukin-6 Levels in Patients with Pancreatic Cancer", Japanese Journal of Clinical Oncology (1998) 28, 1:12-15.
Kannagi, et al. "Quantitative and Qualitative Characterization of Human Cancer-associated Serum Glycoprotein Antigens Expressing Fucosyl or Sialyl-Fucosyl Type 2 Chain Polylactosamine", Cancer Research (1986) 46:2619-2626.
Alonzo, et al. "Sample size calculations for comparative studies of medical tests for detecting presence of disease" Statistics in Medicine (2002) 21(6):835-52.
Anderson, N., et al. "The human plasma proteome: history, character, and diagnostic prospects". Molecular & Cellular Proteomics: MCP (2002) 1(11):845-67.
Arlt, A., et al. "Targeting apoptosis pathways in pancreatic cancer" Cancer letters (2013) 332(2):346-58.
Bauden, M., et al. "Circulating nucleosomes as epigenetic biomarkers in pancreatic cancer" Clin Epigenet (2015) 7: 106.
Bellone, et al., "Tumor-Associated Transforming Growth Factor-b and Interleukin-10 Contribute to a Systemic Th2 Immune Phenotype in Pancreatic Carcinoma Patients" Am J Pathol (1999) 155(2):537-47.
Chang, et al. "LIBSVM: a library for support vector machines" (2018) available at http://www.csie.ntu.edu.tw/~cjlin/ibsvm.
Better, et al. "*Escherichia coli* Secretion of an Active Chimeric Antibody Fragment" Science (1988) 240:1041-3.
Biankin, A., et al. "Molecular pathogenesis of precursor lesions of pancreatic ductal adenocarcinoma" Pathology, (2003) 35(1):14-24.
Bird, et al., "Single-Chain Antigen-Binding Proteins" Science (1988) 242:423-6.
Boeck, S., et al. "Prognostic and therapeutic significance of carbohydrate antigen 19-9 as tumor marker in patients with pancreatic cancer" Oncology (2006) 70(4):255-264.
Borrebaeck, C., et al. "Design of high-density antibody microarrays for disease proteomics: key technological issues" Journal of Proteomics (2009) 72(6):928-35.
Borrebaeck, C., et al. "High-throughput proteomics using antibody microarrays: an update" Expert Rev Mol Diagn (2007) 7:673-86.
Borrebaeck, C. "Antibody Microarray-based Oncoproteomics" Expert Opin. Biol. Ther (2006) 6(8):833-8.

Brand, R., et al. "Serum biomarker panels for the detection of pancreatic cancer" Clinical Cancer Research: An Official Journal of the American Association for Cancer Research (2011) 17(4):805-16.
Bunger, S., et al. "Serum biomarkers for improved diagnostic of pancreatic cancer: a current overview" Journal of Cancer Research and Clinical Oncology (2011) 137(3):375-89.
Burges, et al., "A Tutorial on Support Vector Machines for Pattern Recognition" Data Mining and Knowledge Discovery (1998) 2:121-167.
Carlsson, A., et al. "Plasma proteome profiling reveals, biomarker patterns associated with prognosis and therapy selection in glioblastoma multiforme patients" Proteomics Clinical applications (2010) 4(6-7): 591-602.
Carlsson, A., et al. "Serum proteome profiling of metastatic breast cancer using recombinant antibody microarrays" Eur J Cancer. (2008) 44(3):472-80.
Carlsson, A., et al. "Molecular serum portraits in patients with primary breast cancer predict the development of distant metastases" Proceedings of the National Academy of Sciences of the United States of America (2011) 108(34):14252-7.
Carlsson, A., et al. "Serum protein profiling of systemic lupus erythematosus and systemic sclerosis using recombinant antibody microarrays" Molecular & cellular proteomics (2011) 10(5):M110 005033.
Chang, S., et al. "Identification of a biomarker panel using a multiplex proximity ligation assay improves accuracy of pancreatic cancer diagnosis" J Transl Med., (2009) 7:105.
Chechlinska, M., et al. "Systemic inflammation as a confounding factor in cancer biomarker discovery and validation" Nat Rev Cancer (2010) 10(1):2-3.
Chen, J., et al. "Expression and clinical significance of complement C3, complement C4b1 and apolipoprotein E in pancreatic cancer" Oncology letters (2013) 6(1):43-8.
Seeja, et al., "Identification of co-regulated signature genes in pancreas cancer—a data mining approach" Advanced Intelligent Computing Theories and Applications: With Aspects of Theoretical and Methodological Issues; 4th International Conference on Intelligent Computing, ICIC 2008, Shanghai, China, Sep. 15-18, 2008.
Cheng, et al., "Molecular mechanism for USP7-mediated DNMT1 stabilization by acetylation" Nature Communications (2015) 6(1):7023.
Klein, A.P., et al., "Prospective Risk of Pancreatic Cancer in Familial Pancreatic Cancer Kindreds" (2004) Cancer Res., 64:2634-2638.
Petersen, G.M., "Familial Pancreatic Cancer" (2016) Semin. Oncol., 43(5):548-553.
Trevethan, R., "Sensitivity, Specificity, and Predictive Values: Foundations, Pliabilities, and Pitfalls in Research and Practice" (2017) Front. Public Health, 5:307.
Lignelid, H., et al., "Cystatin C in the human pancreas and gut: an immunohistochemical study of normal and neoplastic tissues" (1992) Virchows Archiv. A Pathol. Anat., 421:491-495.
Zhang, P., et al., "Development of serum parameters panels for the early detection of pancreatic cancer" (2014) Int. J. Cancer, 134:2646-2655.
Kunovsky, L., et al., "The Use of Biomarkers in Early Diagnosis of pancreatic Cancer" (2018) Canadian J. Gastroenter. Hepatol., 2018:5389820.
Kim, J., et al., "Detection of Early Pancreatic Ductal Adenocarcinoma Using Thrombospondin-2 and CA19-9 Blood Markers" (2017) Sci. Transl. Med., 9(398):eaah5583.
Markocka-Maczka, K., "Von Willebrand Factor (vWF) in Plasma of Patients with Pancreatic Carcinoma" (2002) Wspolczesna Onkologia, 6:322-326 [Abstract only].
Muniyan, S., et al., "MUC16 Contributes to the Metastasis of Pancreatic Ductal Adenocarcinoma through Focal Adhesion Mediated Signaling Mechanism" (2016) Genes Cancer, 7:110-124.
Shi, W., et al., "Osteoprotegerin is Up-Regulated in Pancreatic Cancers and Correlates with Cancer-Associated New-Onset Diabetes" (2014) BioScience Trends, 8:322-326.
Nolen, et al., "Prediagnostic Serum Biomarkers as Early Detection Tools for Pancreatic Cancer in a Large Prospective Cohort Study" PLoS ONE (2014) 9(4): e94928.

(56) References Cited

OTHER PUBLICATIONS

Peng, et al., "Predictive proteomic signatures for response of pancreatic cancer patients receiving chemotherapy" Clin. Proteom. (2019) 16:31.

Peng, et al., "Systemic Proteome Alterations Linked to Early Stage Pancreatic Cancer in Diabetic Patients" Cancers (2020) 12:1534.

Lee, et al., "Identification of Human Complement Factor B as a Novel Biomarker Candidate for Pancreatic Ductal Adenocarcinoma" J. Proteome Res. (2014) 13:4878-4888.

Artinyan, et al., "The anatomic location of pancreatic cancer is a prognostic factor for survival" HPB (2008) 10:371-376.

Diaz-Rodriguez, et al., "Hec1 overexpression hyperactivates the mitotic checkpoint and induces tumor formation in vivo" PNAS (2008) 105(43):16719-16724.

Gerdtsson, et al., "Plasma protein profiling in a stage defined pancreatic cancer cohort—Implications for early diagnosis" Mol. Oncol. (2016) 10:1305-1316.

Imai, et al., "Development of diagnostic method for intractable breast cancer and pancreatic cancer using new biomarker PRDM14" (2014) available at https://app.dimensions.ai/details/grant/grant.9493967.

\* cited by examiner

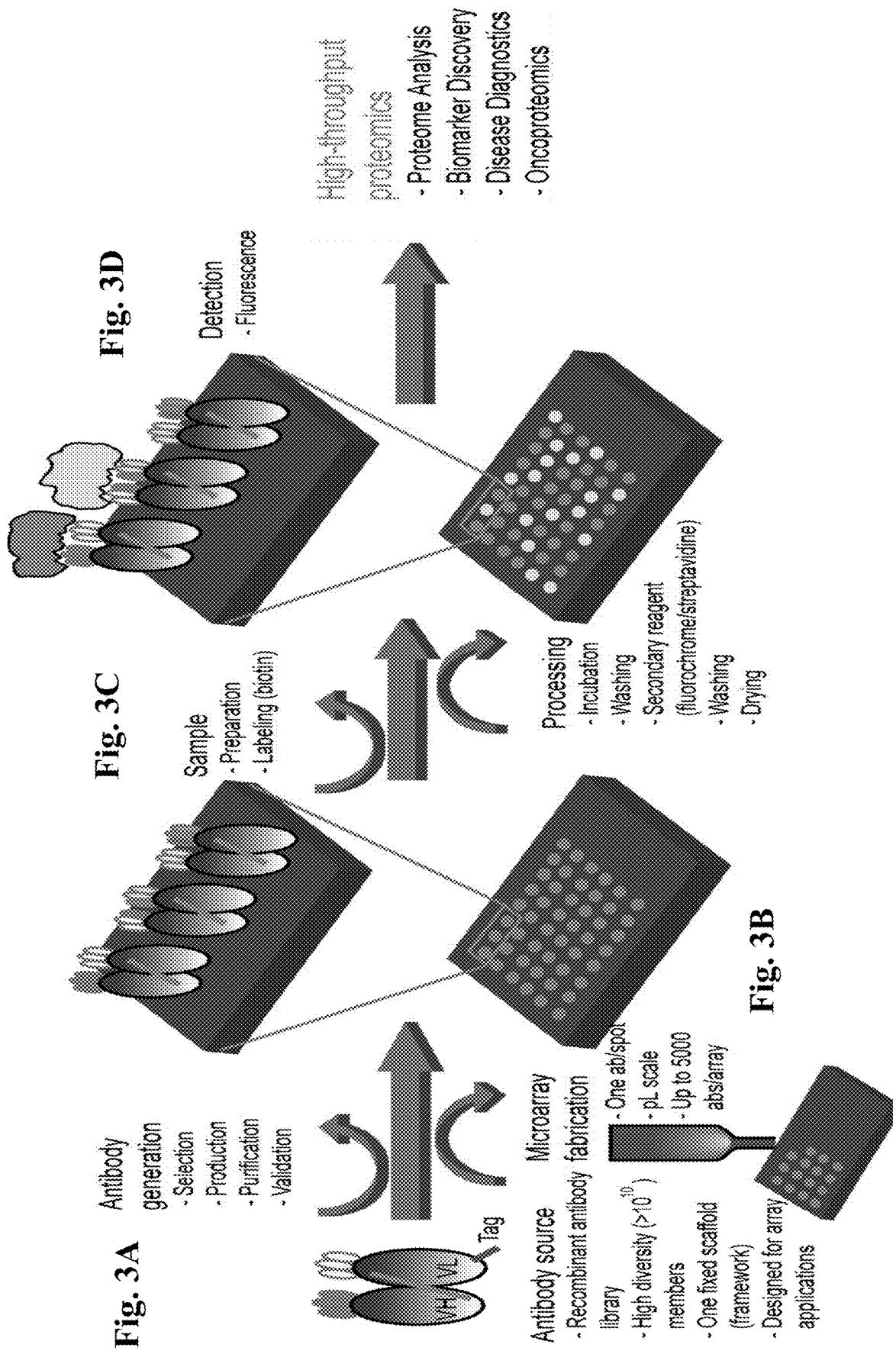

PROTEIN SIGNATURE/MARKERS FOR THE DETECTION OF ADENOCARCINOMA

The present application is a continuation of U.S. patent application Ser. No. 15/589,084, filed May 8, 2017, which is a continuation of U.S. patent application Ser. No. 12/593, 448, filed Sep. 28, 2009, which is a § 371 application of International Patent Application No. PCT/GB2008/001090, filed Mar. 25, 2008, which claims priority to GB Patent Application Nos. 0705876.1, filed Mar. 27, 2007, and 0712181.7, filed Jun. 25, 2007, the entire disclosure of each being incorporated by reference herein.

FIELD OF INVENTION

The present invention relates to methods for diagnosis of pancreatic adenocarcinoma, and biomarkers and arrays for use in the same.

BACKGROUND

One of the remaining challenges in oncology is the ability to stratify patients, relating to their probability to experience tumor relapse or drug treatment resistance, or to their survival expectancy.

Pancreatic ductal adenocarcinoma is the most lethal malignancy by anatomic site, with >30,000 new cases and deaths annually in the United States alone, and with a 5-year survival of 3-5%. This extreme mortality is due to the lack of effective early diagnostic methods (5) and to poor efficacy of existing therapies for advanced disease. Even the patients (10-20%) diagnosed with a surgically resectable tumor, ultimately die of recurrent and metastatic disease. An increased ability to detect and predict cancer is therefore crucial for individual patient management.

Antibody microarray technology (3) has the potential to provide a highly multiplexed analysis (6,7) and has been suggested as the technology platform that eventually will deliver a defined protein signature, i.e. a combination of serum proteins that distinguish cancer from normal patients. Microarray technology has now matured to the point were the initial hurdles have been overcome and minute amounts of proteins in complex proteomes can be analyzed (8-12). However, gene expression profiling of cancer has only demonstrated the ability to predict time of survival in few cases (1,2) and no combination of serum proteins has so far been associated with any of the above clinical parameters.

A serum sample analysis that can predict survival time would allow a more individualized cancer therapy. This has been emphasized for e.g. pancreatic adenocarcinomas, where no tumor-specific markers exist—although most patients will have an elevated CA 19-9 at time of diagnosis, individual prognostic markers have shown to be inconclusive (4). Furthermore, non-invasive approaches, such as computed tomography, is not sufficiently sensitivity to detect small cancers, whereas e.g. endoscopic ultrasonography can be used to survey at-risk individuals for pancreatic lesions (5).

Against this background, the inventors have now developed a proteomic approach to prognostic diagnosis of cancer and identified the first sets of serum biomarkers for detection of pancreatic cancer and for predicting survival.

SUMMARY OF THE INVENTION

Accordingly, in a first aspect, the invention provides a method for determining the presence of pancreatic adenocarcinoma in an individual comprising the steps of:

a) providing a protein sample to be tested (e.g. serum or plasma);

b) determining a protein signature of the test sample by measuring the presence and/or amount in the test sample of one or more proteins selected from the group defined in Table 1;

wherein the presence and/or amount in the test sample of one or more proteins selected from the group defined in Table 1 is indicative of the presence of pancreatic adenocarcinoma.

By "protein signature" we include the meaning of a combination of the presence and/or amount of serum proteins present in an individual having cancer and which can be distinguished from a combination of the presence and/or amount of serum proteins present in an individual not afflicted with cancer (such as pancreatic adenocarcinoma)— i.e. a normal, or healthy, individual.

As exemplified in the accompanying Examples, the presence and/or amount of certain serum proteins present in a test sample may be indicative of the presence of cancer, such as pancreatic adenocarcinoma, in an individual. For example, the relative presence and/or amount of certain serum proteins in a single test sample may be indicative of the presence of cancer, such as pancreatic adenocarcinoma, in an individual.

Preferably, the individual is a human, but may be any mammal such as a domesticated mammal (preferably of agricultural or commercial significance including a horse, pig, cow, sheep, dog and cat).

Preferably, the method of the first aspect of the invention further comprises the steps of:

providing a control serum or plasma sample from an individual not afflicted with pancreatic adenocarcinoma;

d) determining a protein signature of the control sample by measuring the presence and/or amount in the control sample of the one or more proteins measured in step (b);

wherein the presence of pancreatic adenocarcinoma is identified in the event that the presence and/or amount in the test sample of the one or more proteins measured in step (b) is different from the presence and/or amount in the control sample of the one or more proteins measured in step (b).

Preferably, the presence and/or amount in the test sample of the one or more proteins measured in step (b) is significantly different (i.e. statistically different) from the presence and/or amount in the control sample of the one or more proteins measured in step (b). For example, as discussed in the accompanying Examples, significant difference between the presence and/or amount of a particular protein in the test and control samples may be classified as those where $p<0.05$.

Typically, the method of the first aspect comprises measuring the presence and/or amount in the test sample of all of the proteins defined in Table 1—i.e. all 19 of the proteins in Table 1.

Alternatively, the method of the first aspect may comprise measuring the presence and/or amount in the test sample of 1 or 2 or 3 or 4 or 5 or 6 or 7 or 8 or 9 or 10 or 11 or 12 or 13 or 14 or 15 or 16 or 17 or 18 or 19 of the proteins defined in Table 1.

In a preferred embodiment, the method of the first aspect comprises measuring the presence and/or amount in the test sample of Rantes and/or Eotaxin and/or El and/or TNF-b(1) and/or TNF-b(2) and/or GLP-1 and/or VEGF and/or IL-13 and/or CD40.

In a second aspect, the invention provides a method for determining the survival time of an individual afflicted with pancreatic adenocarcinoma comprising the steps of:
i) providing a serum or plasma sample to be tested;
ii) determining a protein signature of the test sample by measuring the presence and/or amount in the test sample of one or more proteins selected from the group defined in Table 2;
wherein the survival time of an individual is identified in the event that the presence and/or amount in the test sample of one or more proteins selected from the group defined in Table 2 is indicative of a survival time of less than 12 months or longer than 12 months or longer than 24 months.

Preferably, the method according to the second aspect further comprises the steps of:
iii) providing a first control serum or plasma sample from an individual having a survival time of less than 12 months and/or a second control serum or plasma sample from an individual having a survival time longer than 12 months and/or longer than 24 months;
iv) determining a protein signature of the first and/or the second control sample by measuring the presence and/or amount of the one or more proteins measured in step (ii);
wherein the survival time of an individual is identified by comparing the presence and/or amount of the one or more proteins in the test sample measured in step (ii) with the presence and/or amount of the one or more proteins in the first and/or second control sample measured in step (iv).

By comparing the presence and/or amount of the selected one or more proteins in the test sample and the control sample, it is possible to determine the survival time of the individual afflicted with pancreatic adenocarcinoma. For example, if the test sample has the same (i.e. identical) or substantially similar or significantly similar presence and/or amount of the selected one or more proteins as a control sample from a patient known to have a survival time of more than 24 months, the test sample will be determined as a sample from a patient having a survival time of more than 24 months. Other such comparisons will be understood by a person skilled in the art of diagnostics.

Typically, the method of the second aspect comprises measuring the presence and/or amount in the test sample of all of the proteins defined in Table 2—i.e. all 22 of the proteins in Table 2.

Alternatively, the method of the first aspect may comprise measuring the presence and/or amount in the test sample of 1 or 2 or 3 or 4 or 5 or 6 or 7 or 8 or 9 or 10 or 11 or 12 or 13 or 14 or 15 or 16 or 17 or 18 or 19 or 20 or 21 or 22 of the proteins defined in Table 2.

In a preferred embodiment, the method of the first aspect comprises measuring the presence and/or amount in the test sample of CD40 ligand and/or mucine and/or IL-16 and/or Rantes and/or Eotaxin and/or MCP-4 and/or IL-11 and/or TNF-b and/or IL-1ra and/or MCP-3 and/or IL-1a and/or IL-3 and/or C3 and/or LDL (1) and/or LDL (2) and/or Lewis Y.

Preferably, the first aspect of the invention provides a method wherein step (b) and/or step (d) is performed using a first binding agent capable of binding to the one or more proteins. Preferably, the second aspect of the invention provides a method wherein step (ii) and/or step (iv) is performed using a first binding agent capable of binding to the one or more proteins.

Binding agents (also referred to as binding molecules) can be selected from a library, based on their ability to bind a given motif, as discussed below.

At least one type, more typically all of the types, of the binding molecules may be an antibody or fragments or variants thereof.

Thus, a fragment may contain one or more of the variable heavy ($V_H$) or variable light ($V_L$) domains. For example, the term antibody fragment includes Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sci. USA 85, 5879) and single domain antibodies (dAbs) comprising isolated V domains (Ward et al (1989) Nature 341, 544).

The term "antibody variant" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecule capable of binding to an antigen in an immunoassay format that is known to those skilled in the art.

A general review of the techniques involved in the synthesis of antibody fragments which retain their specific binding sites is to be found in Winter & Milstein (1991) Nature 349, 293-299.

Additionally or alternatively at least one type, more typically all of the types, of the binding molecules is an aptamer.

Molecular libraries such as antibody libraries (Clackson et al, 1991, Nature 352, 624-628; Marks et al, 1991, J Mol Biol 222(3): 581-97), peptide libraries (Smith, 1985, Science 228(4705): 1315-7), expressed cDNA libraries (Santi et al (2000) J Mol Biol 296(2): 497-508), libraries on other scaffolds than the antibody framework such as affibodies (Gunneriusson et al, 1999, Appl Environ Microbiol 65(9): 4134-40) or libraries based on aptamers (Kenan et al, 1999, Methods Mol Biol 118, 217-31) may be used as a source from which binding molecules that are specific for a given motif are selected for use in the methods of the invention.

The molecular libraries may be expressed in vivo in prokaryotic (Clackson et al, 1991, op. cit.; Marks et al, 1991, op. cit.) or eukaryotic cells (Kieke et al, 1999, Proc Natl Acad Sci USA, 96(10):5651-6) or may be expressed in vitro without involvement of cells (Hanes & Pluckthun, 1997, Proc Natl Acad Sci USA 94(10):4937-42; He & Taussig, 1997, Nucleic Acids Res 25(24):5132-4; Nemoto et al, 1997, FEBS Lett, 414(2):405-8).

In cases when protein based libraries are used often the genes encoding the libraries of potential binding molecules are packaged in viruses and the potential binding molecule is displayed at the surface of the virus (Clackson et al, 1991, op. cit.; Marks et al, 1991, op. cit; Smith, 1985, op. cit.).

The most commonly used such system today is filamentous bacteriophage displaying antibody fragments at their surfaces, the antibody fragments being expressed as a fusion to the minor coat protein of the bacteriophage (Clackson et al, 1991, op. cit.; Marks et al, 1991, op. cit). However, also other systems for display using other viruses (EP 39578), bacteria (Gunneriusson et al, 1999, op. cit.; Daugherty et al, 1998, Protein Eng 11(9):825-32; Daugherty et al, 1999, Protein Eng 12(7):613-21), and yeast (Shusta et al, 1999, J Mol Biol 292(5):949-56) have been used.

In addition, recently, display systems utilising linkage of the polypeptide product to its encoding mRNA in so called ribosome display systems (Hanes & Pluckthun, 1997, op. cit.; He & Taussig, 1997, op. cit.; Nemoto et al, 1997, op.

cit.), or alternatively linkage of the polypeptide product to the encoding DNA (see U.S. Pat. No. 5,856,090 and WO 98/37186) have been presented.

When potential binding molecules are selected from libraries one or a few selector peptides having defined motifs are usually employed. Amino acid residues that provide structure, decreasing flexibility in the peptide or charged, polar or hydrophobic side chains allowing interaction with the binding molecule may be used in the design of motifs for selector peptides. For example
(i) Proline may stabilise a peptide structure as its side chain is bound both to the alpha carbon as well as the nitrogen;
(ii) Phenylalanine, tyrosine and tryptophan have aromatic side chains and are highly hydrophobic, whereas leucine and isoleucine have aliphatic side chains and are also hydrophobic;
(iii) Lysine, arginine and histidine have basic side chains and will be positively charged at neutral pH, whereas aspartate and glutamate have acidic side chains and will be negatively charged at neutral pH;
(iv) Asparagine and glutamine are neutral at neutral pH but contain a amide group which may participate in hydrogen bonds;
(v) Serine, threonine and tyrosine side chains contain hydroxyl groups, which may participate in hydrogen bonds.

Typically selection of binding molecules may involve the use of array technologies and systems to analyse binding to spots corresponding to types of binding molecules.

Preferably, the first binding agent is an antibody or a fragment thereof; more preferably, a recombinant antibody or fragment thereof. Conveniently, the antibody or fragment thereof is selected from the group consisting of: scFv; Fab; a binding domain of an immunoglobulin molecule.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

In a preferred embodiment, the invention provides methods wherein the one or more proteins in the test sample is labelled with a detectable moiety. Preferably, the first aspect provides a method wherein the one or more proteins in the control sample is labelled with a detectable moiety. Alternatively, in the second aspect the one or more proteins in the first and/or second control sample is labelled with a detectable moiety.

By a "detectable moiety" we include the meaning that the moiety is one which may be detected and the relative amount and/or location of the moiety (for example, the location on an array) determined.

Detectable moieties are well known in the art.

A detectable moiety may be a fluorescent and/or luminescent and/or chemiluminescent moiety which, when exposed to specific conditions, may be detected. For example, a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

Alternatively, the detectable moiety may be a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again, $^{131}$I, $^{111}$In, $^{19}$F, $^{13}$C, $^{15}$N, $_{17}$O, gadolinium, manganese or iron. Clearly, the agent to be detected (such as, for example, the one or more proteins in the test sample and/or control sample described herein and/or an antibody molecule for use in detecting a selected protein) must have sufficient of the appropriate atomic isotopes in order for the detectable moiety to be readily detectable.

The radio- or other labels may be incorporated into the agents of the invention (i.e. the proteins present in the samples of the methods of the invention and/or the binding agents of the invention) in known ways. For example, if the binding moiety is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh, $^{188}$Rh and $^{111}$In can, for example, be attached via cysteine residues in the binding moiety. Yttrium-90 can be attached via a lysine residue. The IODOGEN method (Fraker et al (1978) *Biochem. Biophys. Res. Comm.* 80, 49-57) can be used to incorporate $^{123}$I. Reference ("Monoclonal Antibodies in Immunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

The accompanying Examples provide an example of methods and detectable moieties for labelling agents of the invention (such as, for example, proteins in the sample of the methods of the invention and/or binding molecules) for use in the methods of the invention.

Preferably, the detectable moiety is selected from the group consisting of: a fluorescent moiety; a luminescent moiety; a chemiluminescent moiety; a radioactive moiety; an enzymatic moiety.

Preferably, the first aspect provides a method wherein step (b) and/or step (d) is performed using an array. Conveniently, in the second aspect, step (ii) and/or step (iv) is performed using an array.

Arrays per se are well known in the art. Typically they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. By using well-known techniques, such as contact or non-contact printing, masking or photolithography, the location of each spot can be defined. For reviews see Jenkins, R. E., Pennington, S. R. (2001, Proteomics, 2,13-29) and Lal et al (2002, Drug Discov Today 15;7(18 Suppl):S143-9).

Typically the array is a microarray. By "microarray" we include the meaning of an array of regions having a density of discrete regions of at least about 100/cm$^2$, and preferably at least about 1000/cm$^2$. The regions in a microarray have typical dimensions, e.g., diameters, in the range of between about 10-250 μm, and are separated from other regions in the array by about the same distance. The array may also be a macroarray or a nanoarray.

Once suitable binding molecules (discussed above) have been identified and isolated, the skilled person can manufacture an array using methods well known in the art of molecular biology.

Alternatively, the first aspect of the invention provides a method wherein step (b) and/or step (d) is performed using an assay comprising a second binding agent capable of binding to the one or more proteins, the second binding agent having a detectable moiety.

Typically, in the second aspect, step (ii) and/or step (iv) is performed using an assay comprising a second binding agent capable of binding to the one or more proteins, the second binding agent having a detectable moiety.

Binding agents are described in detail above.

In a preferred embodiment, the second binding agent is an antibody or a fragment thereof; typically a recombinant antibody or fragment thereof. Conveniently, the antibody or fragment thereof is selected from the group consisting of: scFv; Fab; a binding domain of an immunoglobulin molecule. Antibodies are described in detail above.

It is preferred that, where an assay is used, the invention provides a method wherein the detectable moiety is selected from the group consisting of: a fluorescent moiety; a luminescent moiety; a chemiluminescent moiety; a radioactive moiety; an enzymatic moiety. Examples of suitable detectable moieties for use in the methods of the invention are described above.

Preferred assays for detecting serum or plasma proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference. Antibody staining of cells on slides may be used in methods well known in cytology laboratory diagnostic tests, as well known to those skilled in the art.

Typically, the assay is an ELISA (Enzyme Linked Immunosorbent Assay) which typically involve the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemi-luminescent systems based on enzymes such as luciferase can also be used.

Conjugation with the vitamin biotin is frequently used since this can readily be detected by its reaction with enzyme-linked avidin or streptavidin to which it binds with great specificity and affinity.

In a third embodiment, the invention provides an array for determining the presence of pancreatic adenocarcinoma in an individual comprising one or more binding agent according to the invention. Preferably, the one or more binding agent is capable of binding to all of the proteins defined in Table 1.

In a fourth embodiment, the invention provides an array for determining the survival time of an individual afflicted with pancreatic adenocarcinoma comprising one or more binding agent according to the invention. Preferably, the one or more binding agent is capable of binding to all of the proteins defined in Table 2.

Arrays suitable for use in the methods of the invention are discussed above. In a further embodiment, the invention provides the use of an array in the methods of the first and/or second aspects of the invention.

In a fifth embodiment, the invention provides the use of one or more proteins selected from the group defined in Table 1 as a diagnostic marker for determining the presence of pancreatic adenocarcinoma in an individual. Conveniently, all of the proteins defined in Table 1 are used as a diagnostic marker for determining the presence of pancreatic adenocarcinoma in an individual.

In a sixth embodiment, the invention provides the use of one or more proteins selected from the group defined in Table 2 as a diagnostic marker for determining the survival time of an individual afflicted with pancreatic adenocarcinoma. It is preferred that all of the proteins defined in Table 2 are used as a diagnostic marker for determining the survival time of an individual afflicted with pancreatic adenocarcinoma.

In a seventh embodiment, there is provided a kit for determining the presence of pancreatic adenocarcinoma comprising:

A) one or more first binding agent or an array according to the invention;

B) instructions for performing the method according to the first aspect of the invention.

In an eighth aspect, the invention provides a kit for determining the presence of pancreatic adenocarcinoma comprising:

A) one or more second binding agent as defined herein

B) instructions for performing the method as defined in the first aspect of the invention.

In a ninth aspect, there is provided a kit for determining the survival time of an individual afflicted with pancreatic adenocarcinoma comprising:

1) one or more first binding agent as defined herein;

2) instructions for performing the method according to the second aspect of the invention.

In a tenth aspect the invention provides a kit for determining the survival time of an individual afflicted with pancreatic adenocarcinoma comprising:

1) one or more second binding agent as defined herein;

2) instructions for performing the method as defined in the second aspect of the invention.

The listing or discussion of a prior-published document in this specification should not necessarily be taken as an acknowledgement that the document is part of the state of the art or is common general knowledge.

Preferred, non-limiting examples which embody certain aspects of the invention will now be described, with reference to the following tables and figures:

TABLE 1

Serum protein profile for distinguishing normal vs. pancreatic cancer patients
Protein analyte Rantes
Eotaxin
IL-12
EI (i.e. C1 esterase inhibitor)
IL-8
MCP-1
TNF-b (1)
TNF-b (2)
GLP-1
VEGF
IL-5
IL-4
IL-13
angiomotin
C4
C3
Factor B
C5
CD40

TABLE 2

Serum protein signature for distinguishing short-term survivors (<12 months) vs. long-term survivors (>24 months) among the pancreatic cancer patients
Protein analyte TGF-b1
CD40 ligand
IL-4
Mucine
IL-16
Rantes
Eotaxin
C5
MCP-4
IL-11
TNF-b
IL-1ra
MCP-3
IL-1a
IL-8
IL-3
C3
Angiomotin
LDL (1)
LDL (2)
Factor B
lewis Y

TABLE 3

129 recombinant antibody fragments, directed against 60 serum proteins, for use in microarray of the invention

| Antigen | scFv clone number | Concentration (µg/ml) |
|---|---|---|
| IL-1a | 1 | 130 |
|  | 2 | 130 |
|  | 3 | 190 |
| Il-1b | 1 | 170 |
|  | 2 | 130 |
|  | 3 | <100 |
| IL-1-ra | 1 | 400 |
|  | 2 | 350 |
|  | 3 | 280 |
| IL-2 | 1 | 140 |
|  | 2 | 160 |
|  | 3 | 110 |
| IL-3 | 1 | 130 |
|  | 2 | 110 |
|  | 3 | <100 |
| IL-4 | 1 | <100 |
|  | 2 | 170 |
|  | 3 | 330 |
|  | 4 | <100 |
| IL-5 | 1 | 110 |
|  | 2 | 120 |
|  | 3 | 130 |
| IL-6 | 1 | 140 |
|  | 2 | <100 |
|  | 3 | 420 |
|  | 4 | 1390 |
| IL-7 | 1 | 140 |
|  | 2 | <100 |
| IL-8 | 1 | 370 |
|  | 2 | 220 |
|  | 3 | 850 |
| IL-9 | 1 | 140 |
|  | 2 | 510 |
|  | 3 | 220 |
| IL-10 | 1 | 130 |
|  | 2 | <100 |
|  | 3 | 120 |
| IL-11 | 1 | 660 |
|  | 2 | 310 |
|  | 3 | 320 |
| IL-12 | 1 | 300 |

TABLE 3-continued 129 recombinant antibody fragments, directed against 60 serum proteins, for use in microarray of the invention

| Antigen | scFv clone number | Concentration (µg/ml) |
|---|---|---|
|  | 2 | 170 |
|  | 3 | 110 |
|  | 4 | 220 |
| IL-13 | 1 | 250 |
|  | 2 | 250 |
|  | 3 | 150 |
| IL-16 | 1 | <100 |
|  | 2 | <100 |
|  | 3 | 160 |
| IL-18 | 1 | 100 |
|  | 2 | 160 |
|  | 3 | 420 |
| TGF-b1 | 1 | 320 |
|  | 2 | 400 |
|  | 3 | 280 |
| TNF-a | 1 | 410 |
|  | 2 | 250 |
|  | 3 | 120 |
| TNF-b | 1 | 180 |
|  | 2 | 180 |
|  | 3 | 530 |
|  | 4 | 290 |
| INF-g | 1 | 320 |
|  | 2 | 110 |
|  | 3 | 330 |
| VEGF | 1 | 160 |
|  | 2 | 270 |
|  | 3 | 400 |
|  | 4 | 140 |
| Angiomotin | 1 | 510 |
|  | 2 | 1380 |
| MCP-1 | 1 | <100 |
|  | 2 | 420 |
|  | 3 | 210 |
| MCP-3 | 1 | <100 |
|  | 2 | 150 |
|  | 3 | <100 |
| MCP-4 | 1 | 790 |
|  | 2 | <100 |
|  | 3 | 420 |
| Eotaxin | 1 | <100 |
|  | 2 | 190 |
|  | 3 | <100 |
| RANTES | 1 | 350 |
|  | 2 | 130 |
|  | 3 | <100 |
| GM-CSF | 1 | 150 |
|  | 2 | 170 |
|  | 3 | 280 |
| CD40 | 1 | 1910 |
|  | 2 | 1290 |
|  | 3 | 450 |
|  | 4 | 920 |
| GLP-1 | 1 | 280 |
| GLP-1-R | 1 | 140 |
| C1q | 1 | 470 |
| C1s | 1 | 530 |
| C3 | 1 | 1110 |
|  | 2 | 170 |
| C4 | 1 | 390 |
| C5 | 1 | 470 |
|  | 2 | 1000 |
| Factor B | 1 | 220 |
| B6 | 2 | 370 |
| Properdin | 1 | 1300 |
| Esterase inhibitor | 1 | 650 |
| CD40 ligand | 1 | 880 |
| PSA | 1 | 400 |
| Leptin | 1 | 160 |
| LDL | 1 | 130 |
|  | 2 | 670 |
| Integrin alpha-10 | 1 | <100 |
| Integrin alpha-11 | 1 | 240 |
| Procathepsin | 1 | 530 |

TABLE 3-continued 129 recombinant antibody fragments, directed against 60 serum proteins, for use in microarray of the invention

| Antigen | scFv clone number | Concentration (µg/ml) |
|---|---|---|
| Tyrosine-protein kinase BTK | 1 | 590 |
| Tyrosine-protein kinase JAK3 | 1 | 130 |
| B-lactamase | 1 | 360 |
| Lewis$^x$ | 1 | 580 |
|  | 2 | 280 |
| Lewis$^y$ | 1 | 710 |
| B cell lymphoma sAg | 1 | 630 |
| Sialo Lewis$^x$ | 1 | 140 |
| MUC-1 | 1 | <100 |
| Streptavidin (control) | 1 | 390 |
| Digoxin (control) | 1 | 210 |
| FITC (control) | 1 | 250 |
| TAT (Control) | 1 | 550 |
|  | 2 | 500 |

TABLE 4

Patient demographics

| | | | Age | |
|---|---|---|---|---|
| Class | n | Sex | Mean (SD) | Range |
| PC* | 11 | M | 74 (8) | 60-85 |
|  | 14 | F | 69 (14) | 31-82 |
| Normal | 18 | M | 49 (23) | 22-85 |
|  | 2 | F | 28 (1) | 27-29 |
| All | 45 | M/F | 61 (21) | 22-85 |

*PC = pancreatic adenocarcinoma

BRIEF DESCRIPTION OF THE DRAWINGS

(FIG. 1A) A scanned antibody microarray image containing 1280 data points; (FIG. 1B) A multidimensional analysis represented as an unsupervised Sammon plot based on all 129 antibody fragments, where cancer patients (filled circles) are shown to be completely separated from healthy individuals (open circles); (FIG. 1C) A dendrogram, where cancer patients (PA) are completely separated from normal individuals (N); The two-way hierarchical clustering was based on 19 serum biomarkers that were significantly ($p<0.05$) differentially expressed in cancer vs. normal individuals, using a training set composed of 28 serum samples. Subsequently, a test set of 16 serum samples (marked with *) were 100% correctly classified. Columns represents donors, normal individuals (N) and cancer patients (PA). Each row represents a serum biomarker, as denoted on the right hand side, where each pixel demonstrates the expression level of that particular biomarker in each donor (overexpression, underexpression or no change (black) in pancreatic cancer sera vs. normal sera.); (FIG. 1D) Several of the serum biomarkers, such as IL-4, IL-5, IL-13, and MCP-3, were also analyzed by ELISA to confirm the microarray results. A representative data set is shown for IL-13, demonstrating that conventional ELISA and antibody microarray analysis generated similar results. The sensitivity of the microarray analysis was equal to or better compared to what was obtained by ELISA (data not shown).

(FIG. 2A) A Receiver Operator Curve (ROC) area as a function of the number of analytes included in a predictive signature, which clearly demonstrates that the two cohorts of survivors could be well discriminated using a signature >29 analytes; (FIG. 2B) The ROC area of a predictive serum biomarker signature, based on 29 antibody identified analytes; (FIG. 2C) A SVM was trained with the biomarker signature chosen by the training set. A test set consisting of 10 randomly chosen patients (samples marked with *) was then classified, using the SVM Prediction Value; (FIG. 2D) A heat map based on the 22 non-redundant serum proteins in the predictive signature. The columns represents cancer patients, with long (>24 months) survivors and short (<12 months) survivors.

FIG. 3A-FIG. 3E: Principle of the recombinant antibody microarray technology, which include antibody generation from a recombinant antibody source (FIG. 3A); microarray fabrication (FIG. 3B); sample preparation and labelling following by processing (FIG. 3C); detection (FIG. 3D); and scanned antibody microarray image (FIG. 3E).

EXAMPLE

Overview

Figure 1A:
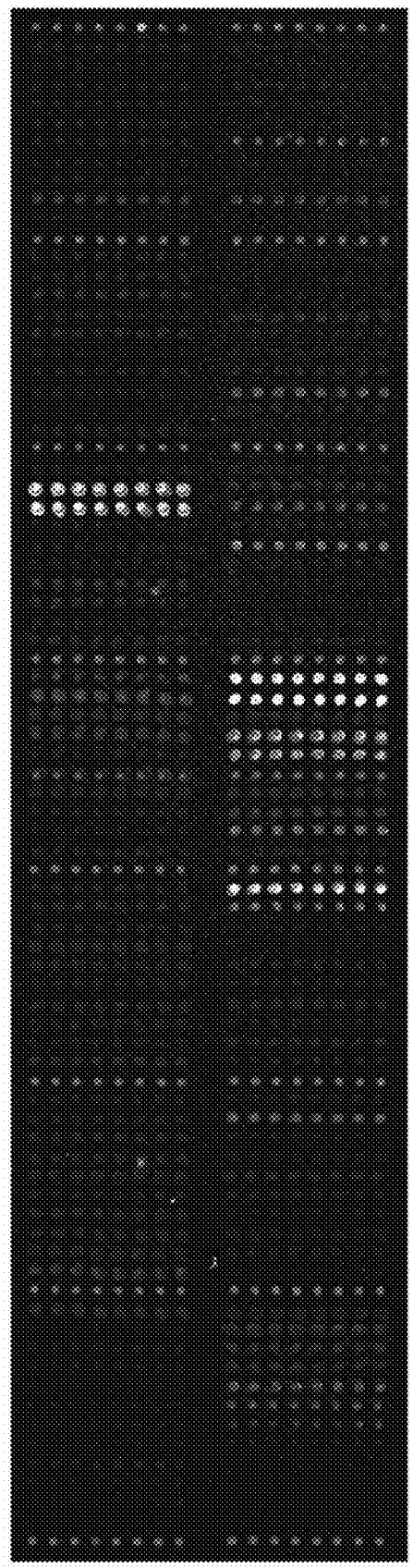
FIG. 1A-FIG. 1D: Detection of pancreatic adenocarcinomas by serum protein expression analysis, using recombinant antibody microarrays.

The driving force behind oncoproteomics is to identify protein signatures that are associated with a particular malignancy. Based on recombinant antibody microarray analysis of unfractionated human whole serum proteomes, derived from pancreatic carcinomas and normal healthy donors, we have identified a protein signature, based on 22 non-redundant analytes, discriminating between cancer and healthy patients. The specificity and sensitivity were predicted to be 99.7 and 99.9%, respectively. Furthermore, a protein signature consisting of 19 protein analytes was defined that had the potential to predicted survival amongst cancer patients. This novel predictor signature distinguished between patients having <12 months or >24 months survival time and suggests new possibilities in individualized medicine.

The present study describes an affinity proteomic approach to prognostic diagnosis of cancer based on a recombinant antibody microarray, utilizing array adapted recombinant scFv fragments (12,13). The results demonstrated that an array of antibody fragments, specific for immunoregulatory proteins, can discriminate between human serum proteomes derived from either cancer patients or healthy individuals. We present the first sets of serum biomarkers for detection of pancreatic cancer as well as for predicting patient survival.

Materials and Methods

Production and purification of scFv—129 human recombinant scFv antibody fragments against 60 different proteins mainly involved in immunregulation, were selected from the n-CoDeR library (13) and kindly provided by BioInvent International AB (Lund, Sweden). Thus, each antigen was recognized by up to four different scFv fragments. All scFv antibodies were produced in 100 ml *E. coli* cultures and purified from expression supernatants, using affinity chromatography on Ni-NTA agarose (Qiagen, Hilden, Germany). Bound molecules were eluted with 250 mM imidazole, extensively dialyzed against PBS, and stored at 4° C., until further use. The protein concentration was determined by measuring the absorbance at 280 nm (average concentration 210 µg/ml, range 60-1090 µg/ml). The purity was evaluated by 10% SDS-PAGE (Invitrogen, Carlsbad, Calif., USA).

Serum Samples—In total, 44 serum samples supplied by Stockholm South General Hospital (Sweden) and Lund University Hospital (Lund, Sweden) were included in this study. 24 serum samples (PA1-PA30) were collected from patients with pancreatic cancer at the time of diagnosis. 20 serum samples (N1-N20) (no clinical symptoms) were collected from healthy donors. Patient demographics are shown in Table 4. All samples were aliquoted and stored at-80° C., following standard operating procedures.

Labeling of serum samples—The serum samples were labeled using previously optimized labeling protocols for serum proteomes (9,14,15). All serum samples were biotinylated using the EZ-Link Sulfo-NHS-LC-Biotin (Pierce, Rockford, Ill., USA). 50 µl serum aliquots were centrifuged at 16.000×g for 20 minutes at 4 ⌷C and diluted 1:45 in PBS, resulting in a concentration of about 2 mg/ml. The samples were then biotinylated by adding Sulfo-NHS-biotin to a final concentration of 0.6 mM for 2 h on ice, with careful Vortexing every 20 minute. Unreacted biotin was removed by dialysis against PBS for 72 hours, using a 3.5 kDa MW dialysis membrane (Spectrum Laboratories, Rancho Dominguez, Calif., USA). The samples were aliquoted and stored at −20° C.

Enzyme linked immunosorbent assay—The serum concentration of 4 protein analytes (MCP-3, IL-4, IL-5 and IL-13) were measured in all samples, using commercial ELISA kits (Quantikine, R&D Systems, Minneapolis, Minn., USA). The measurements were performed according to the recommendations provided by the supplier.

Fabrication and processing of antibody microarrays—For production of the antibody microarrays, we used a set-up previously optimized and validated (9,12,14,15). Briefly, the scFv microarrays were fabricated, using a non-contact printer (Biochip Arrayer, Perkin Elmer Life & Analytical Sciences), which deposits approximately 330 pL/drop, using piezo technology. The scFv antibodies were arrayed by spotting 2 drops at each position and the first drop was allowed to dry out before the second drop was dispensed. The antibodies were spotted onto black polymer MaxiSorb microarray slides (NUNC A/S, Roskilde, Denmark), resulting in an average of 5 fmol scFv per spot (range 1.5-25 fmol). Eight replicates of each scFv clone were arrayed to ensure adequate statistics. In total, 160 antibodies and controls were printed per slide orientated in two columns with 8×80 antibodies per column. To assist the alignment of the grid during the quantification a row containing Cy5 conjugated streptavidin (2 µg/ml) was spotted for every tenth row. A hydrophobic pen (DakoCytomation Pen, DakoCytomation, Glostrup, Denmark) was used to draw a hydrophobic barrier around the arrays. The arrays were blocked with 500 µl 5% (w/v) fat-free milk powder (Semper AB, Sundbyberg, Sweden) in PBS overnight. All incubations were conducted in a humidity chamber at room temperature. The arrays were then washed four times with 400 µl 0.05% Tween-20 in PBS (PBS-T), and incubated with 350 µl biotinylated serum, diluted 1:10 (resulting in a total serum dilution of 1:450) in 1% (w/v) fat-free milk powder and 1% Tween in PBS (PBS-MT) for 1 h. Next, the arrays were washed four times with 400 µl PBS-T and incubated with 350 µl 1 µg/ml Alexa-647 conjugated streptavidin, diluted in PBS-MT for 1 h. Finally, the arrays were washed four times with 400 µl PBS-T, dried immediately under a stream of nitrogen gas and scanned with a confocal microarray scanner (ScanArray Express, Perkin Elmer Life & Analytical Sciences) at 5 µm resolution, using six different scanner settings. The ScanArray Express software V2.0 (Perkin Elmer Life & Analytical Sciences) was used to quantify the intensity of each spot, using the fixed circle method. The local background was subtracted and to compensate for possible local defects, the two highest and the two lowest replicates were automatically excluded and each data point represents the mean value of the remaining four replicates. The coefficient of correlation for intra-assays was >0.99 and for inter-assays >0.96, respectively.

Data normalization—Only non-saturated spots were used for further analysis of the data. Chip-to-chip normalization of the data sets was performed, using a semi-global normalization approach, conceptually similar to the normalization developed for DNA microarrays. Thus, the coefficient of variation (CV) was first calculated for each analyte and ranked. Fifteen % of the analytes that displayed the lowest CV-values over all samples were identified, corresponding to 21 analytes, and used to calculate a chip-to-chip normalization factor. The normalization factor $N_i$ was calculated by the formula $N_i=S_i/\mu$, where $S_i$ is the sum of the signal intensities for the 21 analytes for each sample and p is the sum of the signal intensities for the 21 analytes averaged over all samples. Each data-set generated from one sample was divided with the normalization factor $N_i$. For the intensities, log 2 values were used in the analysis.

Figure 1B:
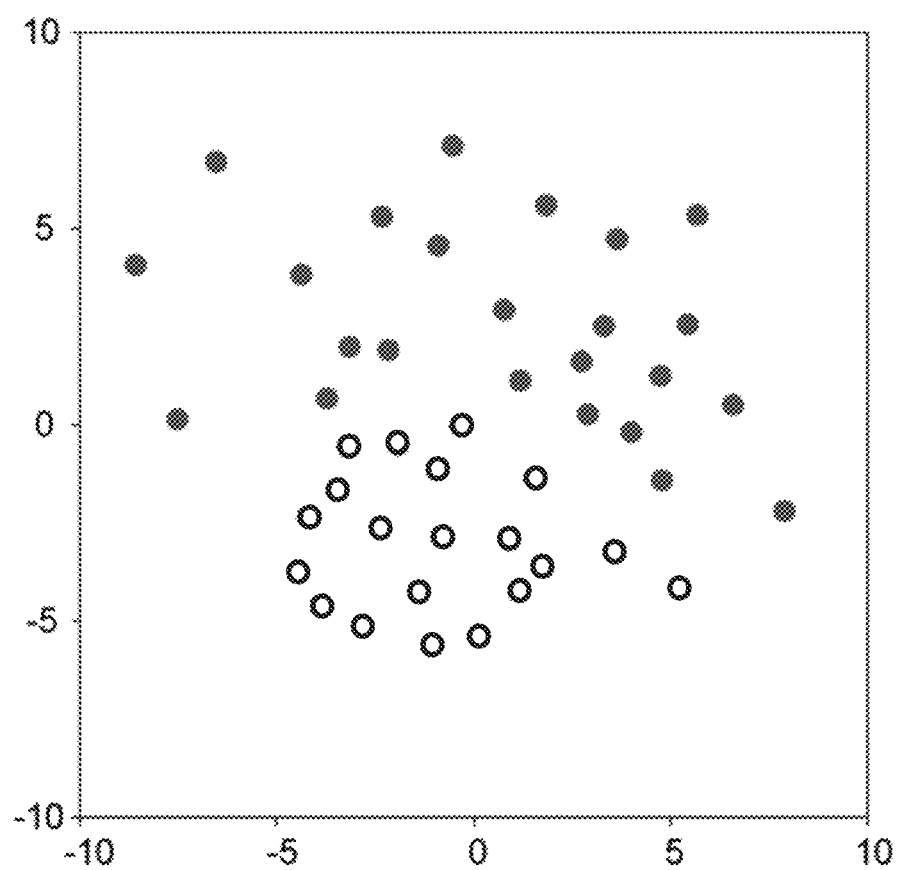
Figure 1C:
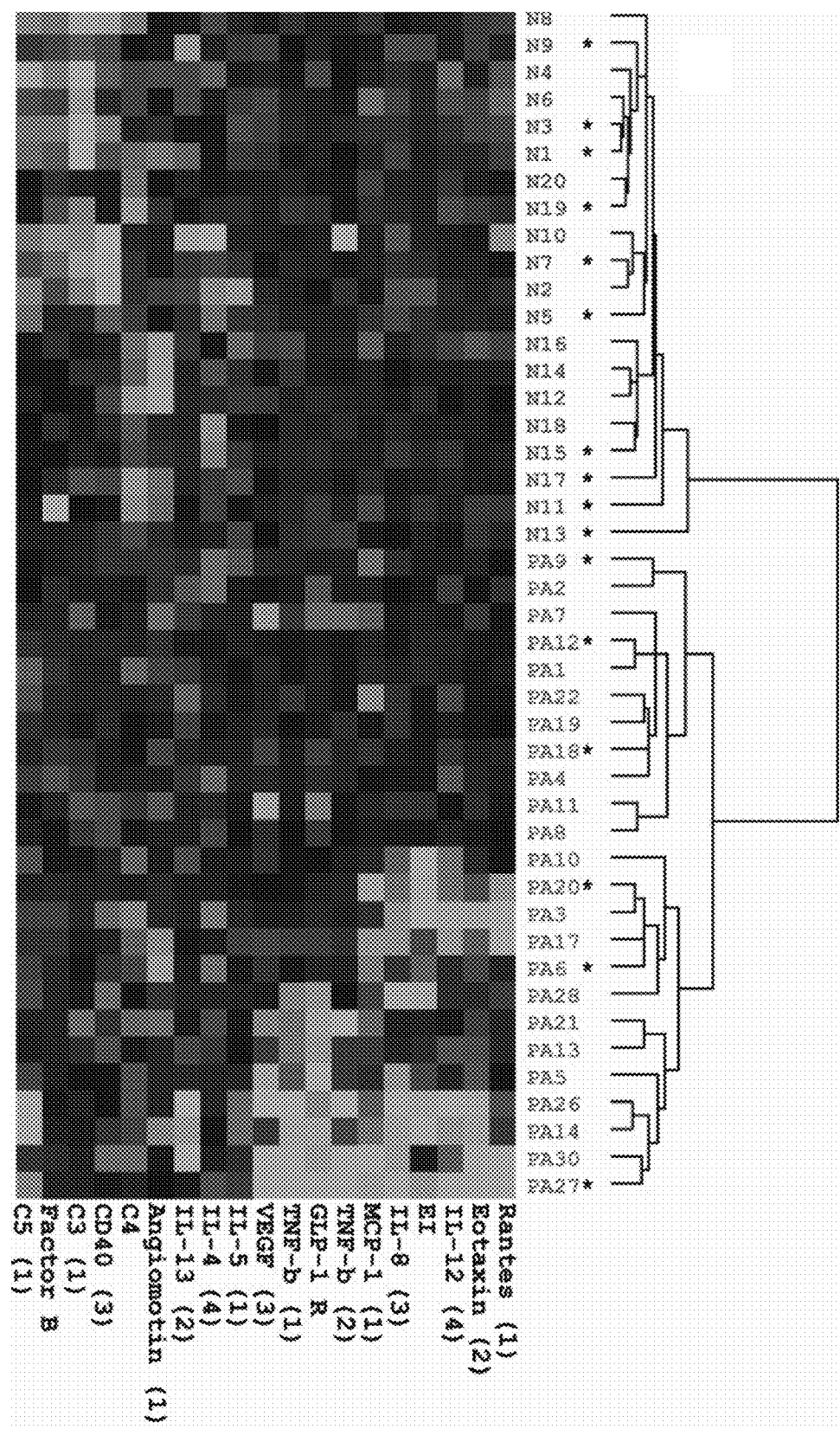
Figure 2A:
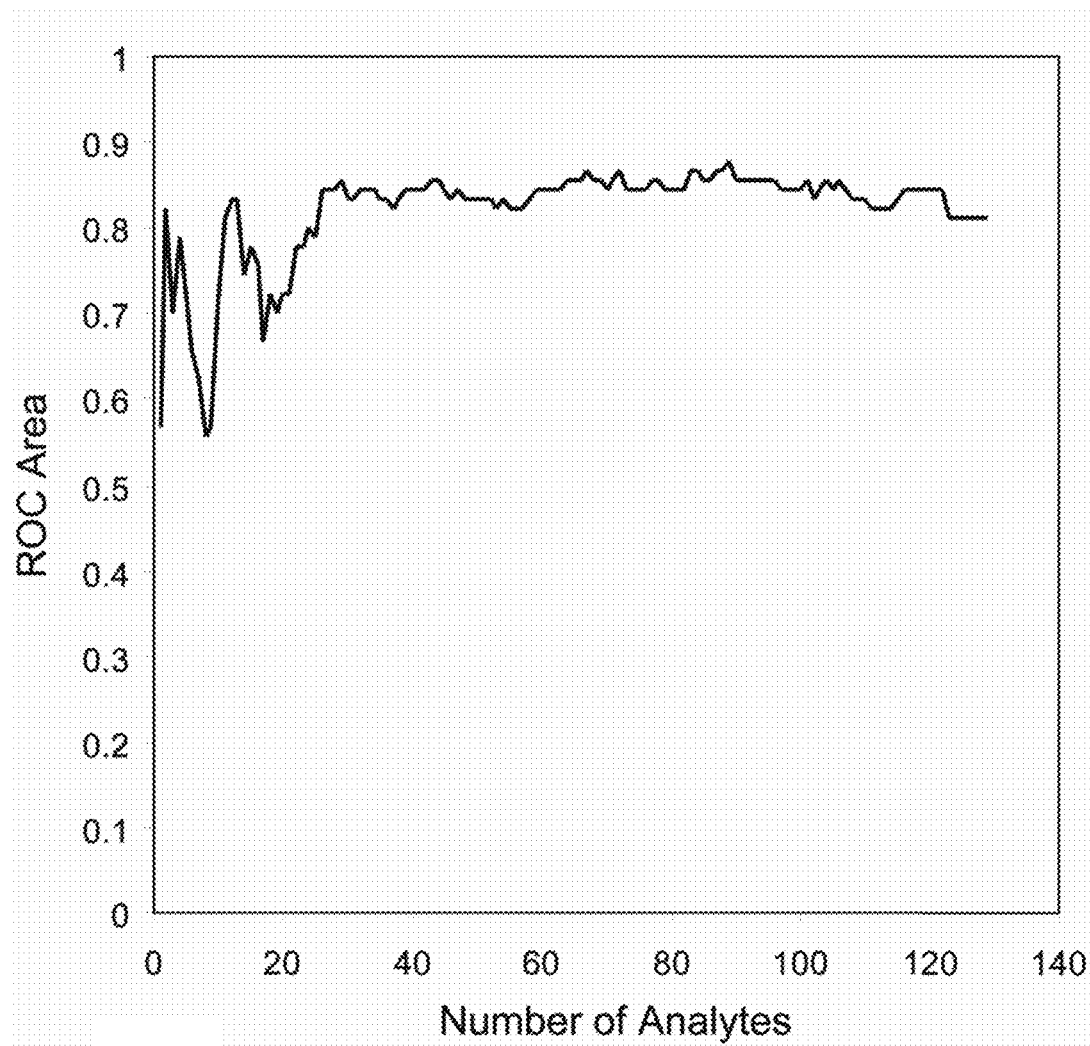
FIG. 2A-FIG. 2D: Identification of a predictive serum protein biomarker signature, discriminating between two patient cohorts of short (<12 months) vs. long (>24 months) survivors.
Figure 2B:
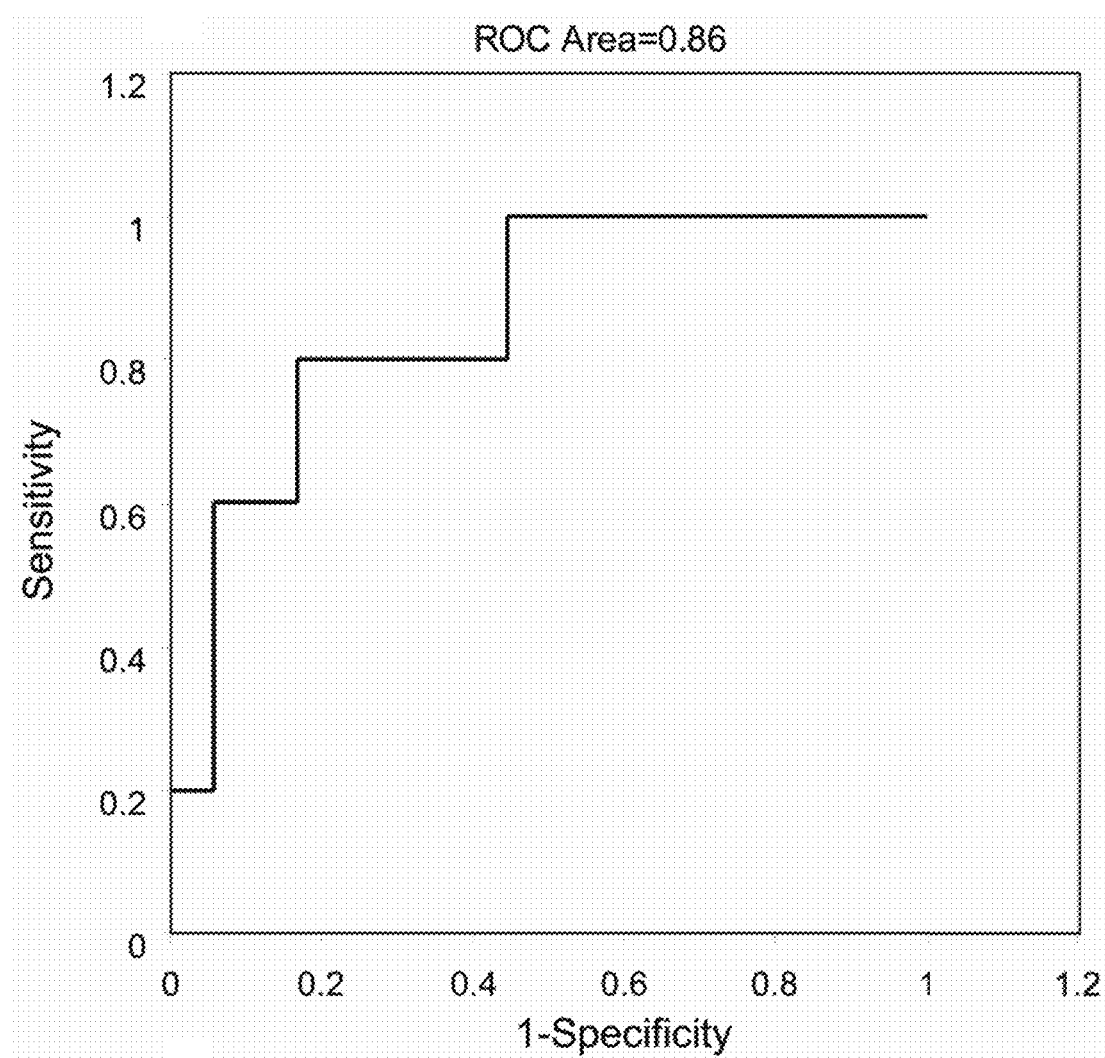
Figure 2C:
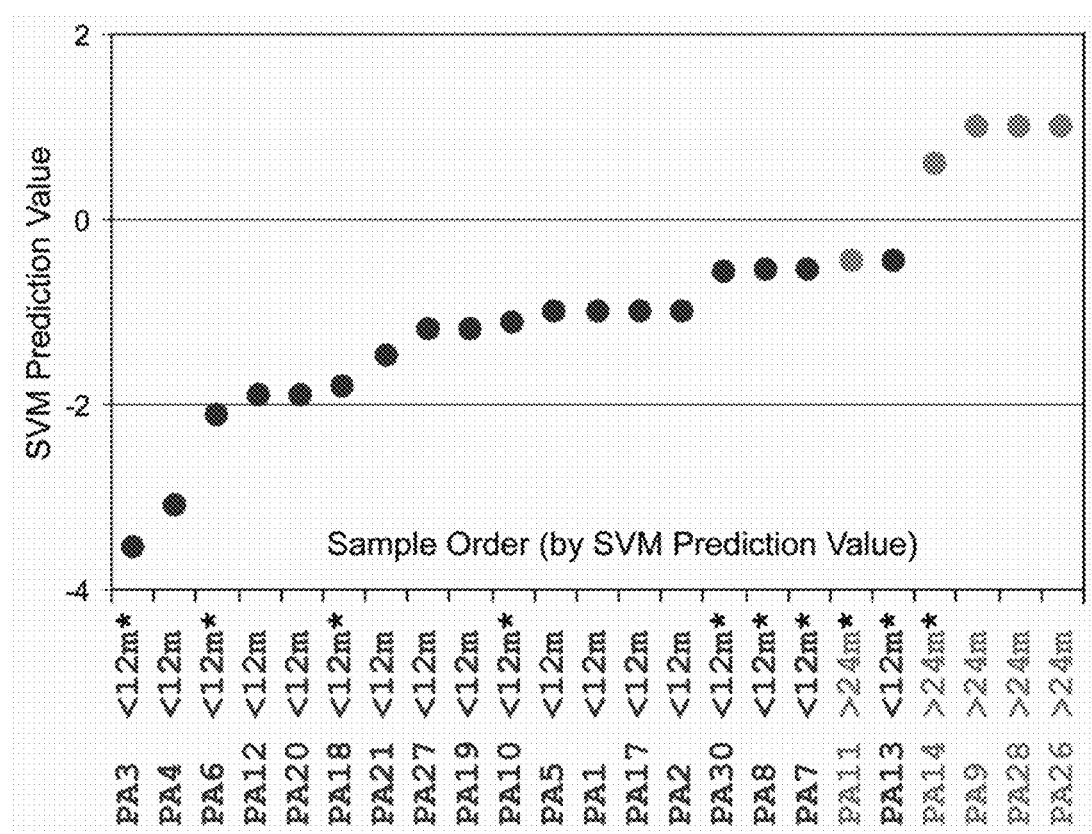

Data analysis—The Sammon map was performed using Euclidean distance in the space of all 129 analytes. Supervised classification was done with a Support Vector Machine (SVM) using a linear kernel (16-18). The cost of constraints violation (the parameter C in the SVM) was fixed to 1, which is the default value in the R function svm, and no attempt was done to tune it. This absence of parameter tuning was chosen to avoid overfitting and to make the classification procedure easier to understand. The output of the SVM on a test sample is a SVM decision value, which is the signed distance to the hyperplane. In FIGS. 1C and 2C, the split into training and test set was done randomly once and kept fixed from thereon. In FIG. 2A, a leave-one-out cross validation procedure is used. For every number K between 1 and 129 the following procedure was carried out. For a training set, i.e., all samples except one, the K highest ranked analytes with a Wilcoxon test were chosen, and a SVM was trained with those K analytes. A SVM decision value was then calculated for the left out sample with this classifier. As is common practice, this was done for all samples in the leave-one-out cross validation.

A Receiver Operating Characteristics (ROC) curve constructed using the SVM decision values and the area under the curve was found. FIG. 2A shows the ROC area as a function of K. FIG. 2B shows the ROC curve for the value K=29. All statistics were done in R (19).

Results

Pancreatic ductal adenocarcinoma is a cancer with poor prognosis and improved diagnostic tool facilitating the clinical decision making would significantly benefit the patients. One approach to improved diagnosis is to identify a set of biomarkers that can detect cancer and that also is predict clinical outcome. Consequently, to be able to identify a protein signature linked to pancreatic cancer with high sensitivity, we have designed the first large-scale microarray (FIG. 1A) based on 129 recombinant antibody fragments (12,14,15), directed against 60 serum proteins, mainly of immunoregulatory nature (Table 2). In this study, labeled sera from 24 pancreatic cancer patients and 20 healthy patients were incubated on the antibody microarrays, which subsequently were quantified, using a confocal scanner. First, to test our ability to detect cancer, the microarray data was displayed in an unsupervised Sammon plot based on all antibodies and two distinct populations could clearly be distinguished (FIG. 1B). This indicated the existence of a clear difference between the cancer and the normal proteomes, in relation to the serum analytes analyzed by the microarray. We subsequently ran a leave-one-out cross-validation, with a Support Vector Machine (SVM), and collected the decision values for each sample. The decision value is the output of the predictor, and samples with a prediction value above (below) a threshold are predicted to be pancreatic carcinomas (healthy). The threshold parameterizes the trade-off between sensitivity and specificity and is often, but not always, set to zero. The 24 pancreatic carcinoma samples obtained decision values in the interval from 0.30 to 1.93, and the healthy samples in the interval from −1.84 to −0.30. Thus, with a threshold value of zero, or any other value between −0.30 and 0.30, the sensitivity and specificity is 100% in our data set. However, to extrapolate the sensitivity and specificity to a larger population, we first verified that the decision values were approximately normally distributed, within the normal vs. cancer groups, respectively and calculated the means and variances. By setting the classification threshold halfway between the two means and using normal distributions, we found a 99.9% sensitivity and 99.3% specificity, which indicated excellent classification power even in a larger population. To illustrate the clear separation between the normal and cancer group, we randomly selected a training set, consisting of 18 cancer and 10 normal samples. This training set of cancer and normal serum proteomes defined a smaller set of biomarkers, consisting of 19 non-redundant serum proteins that differed significantly (p<0.05) between the two samples. These differentially expressed proteins were subsequently used to construct a dendrogram of the 28 training samples and the 16 remaining samples, which were used as a test set. As can be seen in FIG. 10, the cancer samples are completely separated from the normal samples for both the training and test set (100% sensitivity and specificity).

Figure 1D:
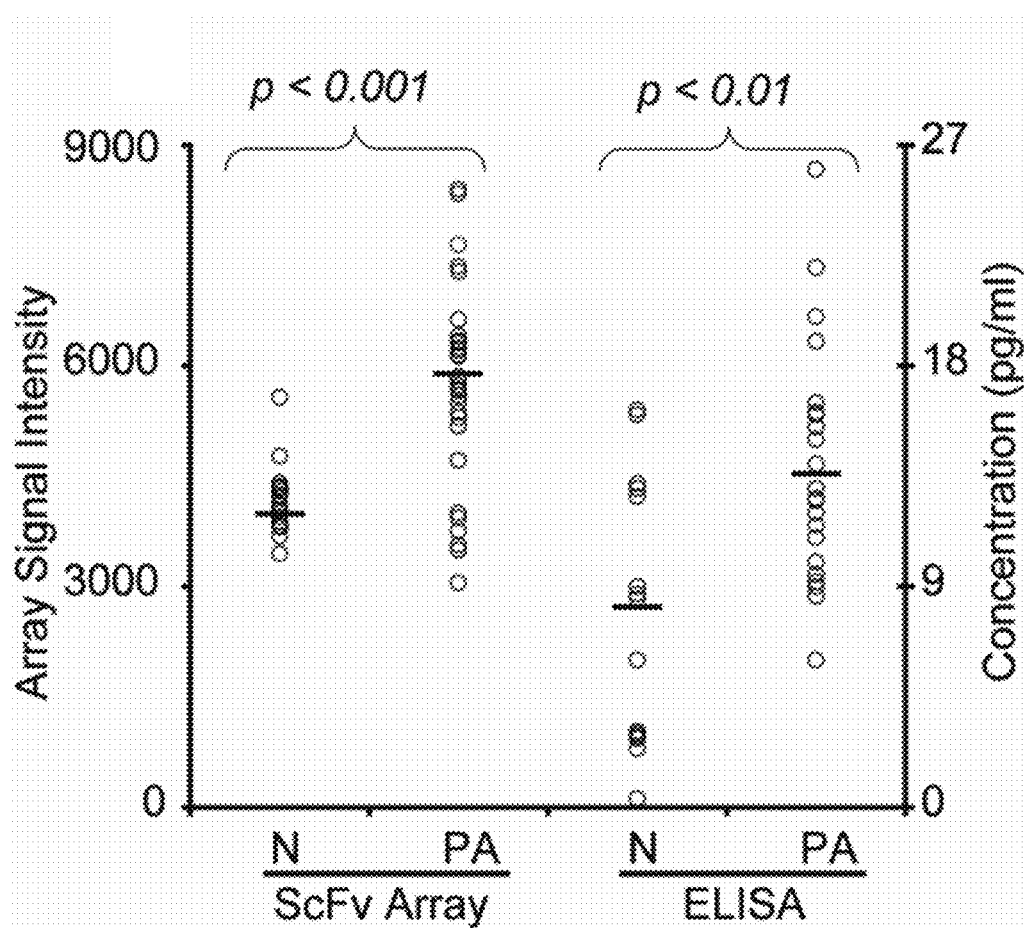

An interesting observation was the fact that we had blindly obtained three serum samples from one patient (PA14), drawn at different occasions a few weeks apart but 11-12 months before that patient was diagnosed with pancreatic cancer. Still, all samples were correctly classified as cancer, when used in the test set (data not shown). Importantly, the protein signature, defined by the training and used for classification of the test samples, is specific for pancreatic adenocarcinomas and differs from serum signatures found by our microarray set-up in other cancers, such as gastric (9) and breast adenocarcinomas (manuscript in preparation). Some of the microarray data was also confirmed by analyzing several of the serum proteins by conventional enzyme linked immunosorbent assay (FIG. 1D). However, analysis based on microarray measurements is often more sensitive, compared to traditional enzyme immunoassays. Consequently, analytes could only be validated when the ELISA sensitive was enough, but then our microarray data was confirmed.

While an early detection of cancer has its merits, especially in pancreatic cancer, serum protein profiling has also been suggested as the approach to define signatures that, apart from classify cancer vs. normal, also could be associated with clinical parameters (16). To be able to predict expected survival time would be of high relevance, since this could influence the therapeutic regimes assigned to each patient. Consequently, to further interrogate our recombinant antibody microarray platform, we compared two cohorts of cancer patients divided into short survivors (<12 months) vs. long survivors (>24 months). First, calculated the area under the receiver operator characteristic (ROC) curves, as a function of the total number of antibody-defined analytes in a predictive signature, using a Wilcoxon test to filter analytes, followed by a Support Vector Machine (FIG. 2A). These calculations included all 129 antibodies and since we had 1 to 4 antibody/serum analyte, a certain redundancy was present in the biomarker size of the predictive signature. From these calculations, it was evident that the two cohorts could be discriminated, with a ROC area (AUC) of >0.80. Of note, this curve also demonstrated that a protein signature consisting of <26 analytes provided a more variable and less robust predictor. Consequently, we chose a predictor signature consisting of 29 analytes, for further analysis. The ROC curve for 29 analytes has an area under the curve of 0.86 (FIG. 2B).

Figure 2D:
Figure 3E:
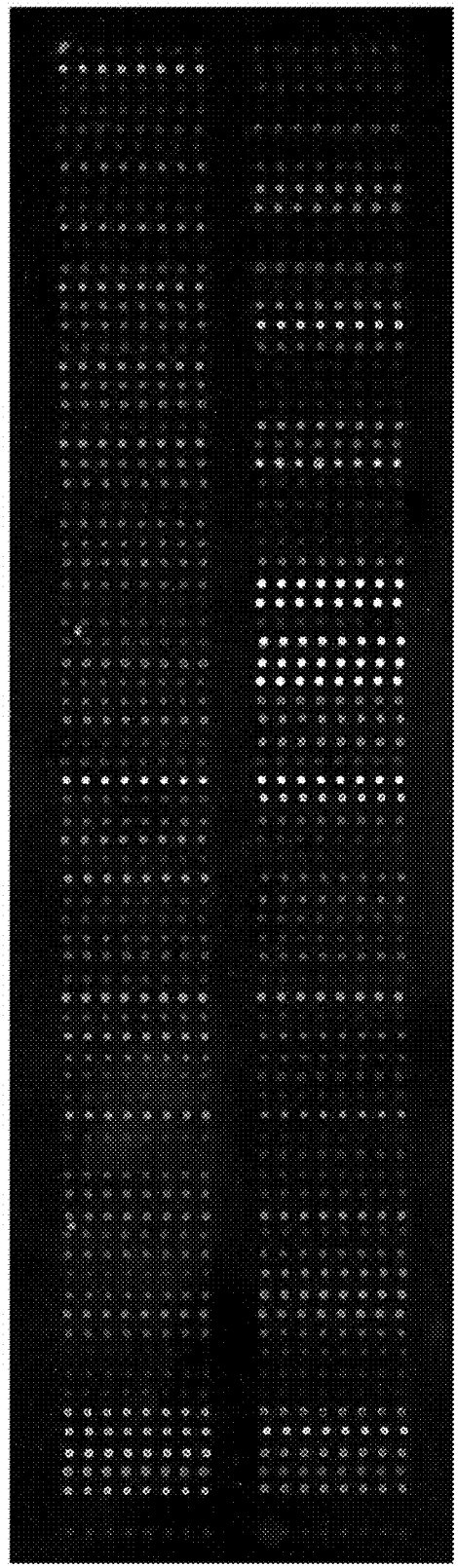

Again, to illustrate the predictive ability of this biomarker signature the pancreatic cancer patients (n=23), comprising the short and long term survivors, were randomly split into a training set of 13 patients and a test set of 10 patients. Since the mean survival for patients with unresectable disease remains 5-6 months there was an inevitable bias in cohort size, and the long-term survivor cohort consisted of only 5 patients. A SVM was trained with the biomarker signature chosen by the training set and the test set could then be classified, as shown in FIG. 2C. All patients surviving <12 months were correctly classified, using a SVM prediction value of <0, which was considered the most important classification. One long-term survivor was missclassified. The 29 most significant analytes separating long and short term survivors among all 23 patients in a Wilcoxon test corresponds to 22 non redundant serum proteins (7 of the 29 analytes were duplicates but defined by different antibody clones). This novel predictor signature, represented by 22 non-redundant proteins, and the differential analyte response displayed by short and long survivors, respectively, are shown as a heat map in FIG. 2D. When analyzing the individual proteins there was no strict consensus patter among the serum proteins, although it was evident that cytokines, such as IL-1a, IL-3, IL-8, and IL-11 were upregulated in short term survivors, while Rantes, IL-16, IL-4 and eotaxin were mostly upregulated in long term survivors (FIG. 2D). The significance of this remains to be validated but it could possibly indicating a more active T-cell compartment in the latter population.

Discussion

Antibody microarrays, as a tool in affinity proteomics, have evolved over the last several years from a promising tool to an approach that is starting to deliver promising results in oncoproteomics (3, 12, 20, 21). The main focus in these endeavors is to detect cancer at an early stage, to predict tumor relapse and treatment resistance, or to select patients for a particular treatment regime (3). This is in particular important for cancers with poor prognosis, which is also intrinsic to pancreatic cancer since it rapidly metastasize to e.g. lymph nodes, lungs, peritoneum (4, 23) and is difficult to diagnose at an early stage. However, the ability of a biomarker signature to distinguish between different carcinomas or between cancer and inflammation has so far been difficult to achieve (for review see ref. 3)(20). The reason for the observed distinction between cancer and normal serum proteomes in this study is most likely dependent on the range of antibody specificities on the microarray, which is also recently supported by the rationally designed array, reported by Sanchez-Carbayo et al. (21). These investigators could stratify patients with bladder tumors on the basis of their overall survival, using antibodies generated against differentially expressed gene products. During the last years, we have developed a high-performing, recombinant antibody microarray platform for complex proteome analysis (6, 9, 11, 12, 14, 15), by evaluating and optimizing key technological parameters (24), such as probe and substrate design (13, 25), array/assay design (9, 15) and sample format (9, 14, 15). This has allowed us to perform the first differential protein expression profiling of the human plasma proteome, using the optimized scFv microarrays, targeting mainly immunoregulatory proteins. In agreement with previous result, this antibody microarrays displayed sensitivities in the pM to fM range, readily detecting low-abundant cytokines. Furthermore, we maintained an assay reproducibility with a coefficient of correlation in the range of 0.96-0.99, which is a key feature of multiplexed analysis and which compares well with previous reports (12, 26). Moreover, the antibody microarray data was compared to ELISA and, when sensitive enough, this conventional assay corroborated our results.

Patients with pancreatic cancer are often diagnosed late, resulting in a poor prognosis. Due to low incidence it is difficult to gather large sample numbers, especially for long-term survivors, i.e. >24 months. We had access to 25 patients for this study, which using a rigorous statistical evaluation still allowed us to classify cancer and normal proteomes. This is a supervised classification and we have employed a Support Vector Machine as the classifier, although we obtained very similar results for this data set with a naive Bayesian classifier (data not shown). The SVM separated the two groups by finding a hyperplane in space of all analytes, and assigned samples on one side of the hyperplane to one of the groups and those on the other side to the other group. The distance to the hyperplane is called the prediction or decision value (FIG. 2C). The hyperplane and, thus, the classification of groups, were found by using our training set. The performance of the classifier was then estimated by subsequently utilizing a test set, where no overlap between the training and test set was allowed. However, a data set can randomly be split into different training and a test set, which are then used to train and test the classifier, respectively. The drawback of this is that the final result depends on the split into training and test set. Consequently, we used cross validation as the procedure of making several splits of our data set and used the average performance of the test sets as a measure of the accuracy of data classification. Thus, in the leave-one-out cross validation that was performed, the test set contains one sample and the training set contains the rest.

The performance of the SVM can be measured by the ROC curve and, in particular, the area under the ROC curve. The normal and pancreatic carcinoma samples were remarkably well separated, since the SVM classified all samples correctly with a gap between the two groups. Extrapolation of the decision values gave very high sensitivity (99.9%) and specificity (99.3%), showing that it would take hundreds of samples to get one misclassification.

In this study, we could not compare the pancreatic cancers with a cohort of patients with pancreatitis, which would have been a desirable comparison, but we instead used normal serum samples. Of note, the present pancreatic cancer associated biomarker signature had, however, only eotaxin, IL-5 and IL-13 in common with fourteen biomarkers found as a result of a bacterial infection, associated with another gastrointestinal cancer (12), which indicated that the pancreatic signature was not related to general inflammation. Furthermore, this signature was not similar to biomarkers found in systemic lupus erythematosus, an autoimmune disorder with a significant inflammatory component (Wingren et al., manuscript in preparation). The signature was also completely different from what Orchekowski et al. reported (26), when profiling pancreatic cancer serum samples, using a microarray based on monoclonal and polyclonal antibodies. They targeted high-abundant serum proteins, such as albumin, transferrin and hemoglobin, as well as more common inflammation markers, such as C-reactive protein (CRP), serum amyloid A and immunoglobulins, whereas only eight cytokines were analyzed. On the other hand, our present cancer signature contained a number of over-expressed TH2 cytokines (IL-4, -5, -10 and -13), whereas classical TH1 cytokines (IL-12 and TNF-b) were down-regulated, which also was in agreement with the study of Belone et al., who showed that TGF-b and IL-10 were up-regulated in pancreatic cancer sera (27). These authors also showed that blood-derived monocytes from pancreatic cancer patients were primed to develop a TH2-like response rather than a TH1-like response, with increased expression of IL-4 and decreased expression of IL-12.

Finally, we investigated the possibility to identify a signature, that apart from being able to classify cancer vs. normal samples, also could be used to predict patient survival. Initially, the SVM could classify the short and long survivors with a ROC area of 0.81, using all analytes (data not shown), which was very promising. Then a classifier was made for every number of biomarkers, by selecting the most significant analytes, which subsequently was used to distinguishing the two sample groups in the training set. As seen in FIG. 2A, the performance of the classifier was stable above 26 analytes, and we could demonstrate that a 29 biomarker (22 non-redundant analytes) signature gave a ROC of 0.86. A study with more than 18 short survivors and 5 long survivors is, however, needed to firmly establish a survival classifying protein profile, but this study certainly establishes the possibility for such a profile.

In conclusion, using a recombinant antibody microarray against immunoregulatory proteins, we have been able to specifically detect pancreatic adenocarcinomas and completely discriminate between cancer vs. normal serum proteomes. More importantly, the first attempt to define a signature capable of predicting survival of cancer patients is presented, indicating the power of affinity oncoproteomics for clinical decision making.

REFERENCES

1. Rosenwald A. et al. *Cancer Cell* 3, 195-197 (2003).
2. van de Vijver, et al. *N. Eng. J. Med* 347, 1999-2009 (2002).
3. Borrebaeck, C.A.K. *Expert Opin. Biol. Ther* 6, 833-838 (2006).
4. Garcea, G., Neal, C. P., Pattenden, C. J., Steward, W. P. & Berry, D. P. *Eur. J. Cancer* 41, 2213-2236 (2005).
5. Yeo, T. P. et al. *Curr. Probl. Cancer* 26, 176-275 (2002).
6. Wingren, C. & Borrebaeck, C. A. K. *Exp. Rev. Proteomics* 1, 355-364 (2004).
7. Pavlickova, P., Schneider, M. E., & Hug, H., *Clin. Chim. Acta* 342, 17-35 (2004).
8. Haab, B. B, et al. *Genome Biol.* 2, 1-13 (2001).
9. Wingren, C., et al., Microarrays based on affinity-tagged single-chain Fv antibodies: sensitive detection of analyte in complex proteomes. *Proteomic* 5, 1281-1291 (2005).
10. Pawlak, M. et al. *Proteomics* 2, 383-393 (2002).
11. Wingren, C. & Borrebaeck, C. A. K. *OM/CS* 3, 411-427 (2006).
12. Ellmark, P., et al., Identification of protein expression signatures associated with *H. pylori* infection and gastric adenocarcinoma using recombinant antibody microarrays. *Mol Cell Proteomics* 5, 1638-1646 (2006).
13. Soderlind, E., et al., Recombining germline-derived CDR sequences for creating diverse single-framework antibody libraries. *Nat. Biotechnol,* 18, 852-856 (2000)
14. Ingvarsson, J.; Larsson, A.; Sjöholm, L.; Truedsson, L.; Jansson, B.; Borrebaeck, C. A. K. and Wingren, C. Design of recombinant antibody microarrays for serum protein profiling: Targeting of complement proteins. *J. Proteome Res.in* press
15. Wingren, C., Ingvarsson, J., Dexlin, L., Szul, D. and Borrebaeck, CAK. Design of recombinant antibody microarrays for complex proteome analysis: choice of sample labelling-tag and solid support. *Proteomics* in press
16. Eisen, M. B., et al., Cluster analysis and display of genome-wide expression patterns. *Proc Natl Acad Sci USA.* 95, 14863-14868 (1998).
17. N. Cristianini and J. Shawe-Taylor, An introduction to support vector machines (and other kernel-based learning methods), Cambridge University Press (2000).
18. Chih-Chung Chang and Chih-Jen Lin, LIBSVM: a library for support vector machines, available at www.c-sie.ntu.edu.tw/~cjlin/libsvm
19. R. Ihaka and R. Gentleman, R: A language for data analysis and graphics, *J. Comp. Graph Stat.* 5, 299-314, (1996)
20. Sanchez-Carbayo, M., Socci, N. D., Lozano, J. J., Haab, B. B. &Cordon-Cardo, C. *Am. J. Pathol.* 168, 93-103 (2006).
21. Schafer, M. W., Mangold, L., Partin, A. W. and Haab, B. B. (2007) Antibody array profiling reveals serum TSP-I as a marker to distinguish benign from malignant prostatic disease, *The Prostate* 67, 255-267.
22. Rustgi, A. K. *Gastroenterology* 129, 1344-1347 (2005).
23. More, G., et al. *Proc. Natl. Acad. Sci (USA)* 102, 7677-7682 (2005).
24. Wingren, C. and Borrebaeck, C. A. K. (2007) nya reviewn
25. Steinhauer, C., et al., Biocompatibility of surfaces for antibody microarrays: design of macroporous silicon substrates. *Anal Biochem* 341, 204-13 (2005)
26. Orchekowski, R., et al., Antibody microarray profiling reveals individual and combined serum proteins associated with pancreatic cancer. Cancer Res. 65, 11193-202 (2005)
27. Bellone, G., et al., Tumor-associated transforming growth factor-beta and interleukin-10 contribute to a systemic Th2 immune phenotype in pancreatic carcinoma patients. Am J Pathol. 155, 537-47 (1999)

The invention claimed is:

1. A method for determining the presence of pancreatic adenocarcinoma in an individual comprising the steps of:
  a) providing a serum or plasma sample to be tested;
  b) determining a protein signature of the test sample by measuring the presence and/or amount in the test sample of the proteins Factor B, Complement 4 (C4), and Complement 5 (C5) ; and
  wherein the presence and/or amount in the test sample of the proteins Factor B, C4, and C5 measured in step (b) is indicative of the presence of pancreatic adenocarcinoma.

2. The method according to claim 1 further comprising the steps of:
  c) providing a control serum or plasma sample from an individual not afflicted with pancreatic adenocarcinoma;

d) determining a protein signature of the control sample by measuring the presence and/or amount in the control sample of the proteins measured in step (b);

wherein the presence of pancreatic adenocarcinoma is identified in the event that the presence and/or amount in the test sample of the proteins measured in step (b) is different from the presence and/or amount in the control sample of the proteins measured in step (b).

3. The method according to claim 1 wherein step (b) is performed using a first binding agent capable of binding to the proteins.

4. The method according to claim 3 wherein the first binding agent is an antibody or a fragment thereof.

5. The method according to claim 1 wherein the proteins in the test sample are labelled with a detectable moiety.

6. The method according to claim 1 wherein step (b) is performed using an array.

7. The method according to claim 1 wherein step (b) is performed using an assay comprising a second binding agent capable of binding to the proteins, the second binding agent having a detectable moiety.

8. The method according to claim 7 wherein the second binding agent is an antibody or a fragment thereof.

9. The method according to claim 1, further comprising:
c) administering a pancreatic cancer therapeutic regime to the individual.

* * * * *